United States Patent
Flynn et al.

(10) Patent No.: US 11,432,805 B2
(45) Date of Patent: Sep. 6, 2022

(54) ESTIMATION AND DISPLAY FOR VECTOR DOPPLER IMAGING USING PLANE WAVE TRANSMISSIONS

(71) Applicant: Verasonics, Inc., Kirkland, WA (US)

(72) Inventors: John Flynn, Seattle, WA (US); Ronald Elvin Daigle, Redmond, WA (US)

(73) Assignee: Verasonics, Inc., Kirkland, WA (US)

( * ) Notice: Subject to any disclaimer, the term of this patent is extended or adjusted under 35 U.S.C. 154(b) by 472 days.

(21) Appl. No.: 16/560,851

(22) Filed: Sep. 4, 2019

(65) Prior Publication Data

US 2019/0388065 A1    Dec. 26, 2019

Related U.S. Application Data

(60) Division of application No. 14/920,778, filed on Oct. 22, 2015, now Pat. No. 10,792,015, which is a continuation of application No. 14/348,007, filed as application No. PCT/US2012/061120 on Oct. 19, 2012, now Pat. No. 9,192,359.

(Continued)

(51) Int. Cl.
| | |
|---|---|
| *A61B 8/00* | (2006.01) |
| *A61B 8/08* | (2006.01) |
| *G01S 15/89* | (2006.01) |
| *A61B 8/06* | (2006.01) |

(Continued)

(52) U.S. Cl.
CPC ............ *A61B 8/5223* (2013.01); *A61B 8/06* (2013.01); *A61B 8/14* (2013.01); *A61B 8/4483* (2013.01); *A61B 8/463* (2013.01); *A61B 8/488* (2013.01); *A61B 8/5207* (2013.01); *A61B 8/5269* (2013.01); *G01S 15/8977* (2013.01);

(Continued)

(58) Field of Classification Search
None
See application file for complete search history.

(56) References Cited

U.S. PATENT DOCUMENTS

| | | |
|---|---|---|
| 4,217,909 A | 8/1980 | Papadofrangakis et al. |
| 5,173,770 A | 12/1992 | Kondo et al. |

(Continued)

FOREIGN PATENT DOCUMENTS

WO    2009/158399 A1    12/2009

OTHER PUBLICATIONS

Bercoff et al., "Ultrafast Compound Doppler Imaging: Providing Full Blood Flow Characterization," *IEEE Transactions on Ultrasonics, Ferroelectics, and Frequency Control* 58(1): 134-147, Jan. 2011.

(Continued)

*Primary Examiner* — Joel F Brutus
(74) *Attorney, Agent, or Firm* — Seed Intellectual Property Law Group LLP

(57) ABSTRACT

Vector Doppler Imaging (VDI) improves on conventional Color Doppler Imaging (CDI) by giving speed and direction of blood flow at each pixel of a display generated by a computing system. Multiple angles of Plane wave transmissions (PWT) via an ultrasound transducer conveniently give projected Doppler measurements over a wide field of view, providing enough angular diversity to identify velocity vectors in a short time window while capturing transitory flow dynamics. A fast, aliasing-resistant velocity vector estimator for PWT is presented, and VDI imaging of a carotid artery with a 5 MHz linear array is shown using a novel synthetic particle flow visualization method.

18 Claims, 13 Drawing Sheets

Related U.S. Application Data

(60) Provisional application No. 61/549,016, filed on Oct. 19, 2011.

(51) Int. Cl.
*A61B 8/14* (2006.01)
*G01F 1/663* (2022.01)

(52) U.S. Cl.
CPC ...... *G01S 15/8984* (2013.01); *G01S 15/8995* (2013.01); *G01F 1/663* (2013.01); *G01S 15/8979* (2013.01)

(56) References Cited

U.S. PATENT DOCUMENTS

| | | |
|---|---|---|
| 5,409,010 A | 4/1995 | Beach et al. |
| 5,454,372 A | 10/1995 | Banjanin et al. |
| 5,587,927 A | 12/1996 | Nagao et al. |
| 5,768,438 A | 6/1998 | Etoh |
| 8,287,456 B2 | 10/2012 | Daigle |
| 2008/0210016 A1 | 9/2008 | Zwirn et al. |
| 2009/0326379 A1 | 12/2009 | Daigle et al. |

OTHER PUBLICATIONS

Flynn et al., "Estimation and Display for Vector Doppler Imaging Using Planewave Transmissions," *IEEE International Ultrasonics Symposium Proceedings*, Orlando, Florida, Oct. 18-21, 2011, pp. 413-418.

Shen et al., "High Frame-Rate Vector Flow Estimation Using Speckle Tracking with Recursive Plane-Wave Compounding," *IEEE Ultrasonics Symposium*, San Diego, California, Oct. 11-14, 2010, pp. 1307-1310.

Udesen et al., "Fast Blood Vector Velocity Imaging: Simulations and Preliminary in vivo Results," *IEEE Ultrasonics Symposium*, New York, New York, Oct. 28-31, 2007, pp. 1005-1008.

Udesen et al., "High Frame-Rate Blood Vector Velocity Imaging Using Plane Waves: Simulations and Preliminary Experiments," *IEEE Transactions on Ultrasonics, Ferroelectrics, and Frequency Control* 55(8):1729-1743, Aug. 2008.

A. Flow region.

B. Particle distribution.

C. Particle forward propagation.

D. Pixel back-propagation.

ESTIMATION AND DISPLAY FOR VECTOR DOPPLER IMAGING USING PLANE WAVE TRANSMISSIONS

BACKGROUND

Technical Field

The present disclosure pertains to ultrasound imaging and, more particularly, to an ultrasound imaging system utilizing velocity vector estimation for generation of a vector Doppler color image in which a synthetic particle flow visualization method is employed.

Description of the Related Art

Ultrasound Imaging has developed into an effective tool for diagnosing a wide variety of disease states and conditions. The market for ultrasound equipment has seen steady growth over the years, fueled by improvements in image quality and the capability to differentiate various types of tissue. Unfortunately, there are still many applications for ultrasound systems where the equipment costs are too high for significant adoption. Examples are application areas such as breast cancer detection, prostate imaging, musculoskeletal imaging, and interventional radiology. In these areas and others, the diagnostic efficacy of ultrasound imaging depends on excellent spatial and contrast resolution for differentiation and identification of various tissue types. These performance capabilities are found only on the more expensive ultrasound systems, which have more extensive processing capabilities.

Ultrasound imaging has always required extensive signal and image processing methods, especially for array systems employing as many as 128 or more transducer elements, each with unique signal processing requirements. The last decade has seen a transition to the improved accuracy and flexibility of digital signal processing in almost all systems except for those at the lowest tiers of the market. This transition has the potential for reducing system costs in the long term by utilizing highly integrated digital circuitry. Unfortunately, the low manufacturing volumes of ultrasound systems results in substantial overhead and fixed costs for these unique circuits, and thus the transition to digital signal processing has not significantly reduced system cost.

Doppler methods in medical ultrasound encompass a number of related techniques for imaging and quantifying blood flow. For stationary targets, the round trip travel time of a pulse reflected from the target back to the transducer is the same for each transmission. Conversely, successive echographic returns from a moving object will arrive at different times with respect to the transmit pulse, and by cross correlating these echoes the velocity of the object can be estimated. Because the ultrasound path is directional (along the beam axis), only axial motion produces a Doppler signal. Flow that is transverse to the beam is not detectable, and thus the velocity magnitudes obtained in conventional Doppler methods represent only the axial component of the flow velocity vector. In order to estimate the true magnitude of the flow velocity vector, Vector Doppler methods are employed. Generally, these methods rely on multiple beam angle data to estimate the direction of the flow vector and the flow velocity vector.

Several Doppler-based methods have been developed to present different aspects of blood flow. Typically, "spatial imaging" of the flow field is used to locate vessels, to measure their size, and to observe flow structure. "Flow imaging" is used in conjunction with echographic imaging in a "duplex" mode that combines both types of images in an overlay, with echographic amplitude presented in grayscale and flow velocity rendered in color. The flow field is computed within a region of interest (ROI) that is a subset of the larger echographic image, because flow imaging is more demanding in both acquisition time and processing load.

Detailed quantification of flow velocity is possible within a much smaller sample volume chosen within the ROI. The smallest volume that can be sampled and processed independently is given by the axial length (the transmit pulse length) and the lateral beam widths (in and out of the imaging plane). Spatial resolution of any method depends on the size of the sample volume and also on the system sensitivity settings for that location.

The Spectral Doppler method reports the spectrum of flow velocity and how it varies over the cardiac cycle, and it usually presents the spectrum graphically as a spectrogram and audibly through loudspeakers. Moreover, the Spectral Doppler method computes the power spectrum of flow velocity obtained over a sequence of transmissions, and usually presents the spectrum graphically as a spectrogram and audibly through loudspeakers. Access to the full time-varying spectrum of blood velocities allows accurate calculation of mean and peak flow velocities within the sample region and provides the most complete characterization of flow disturbances of all the ultrasound Doppler methods.

Color Flow Doppler imaging of the velocity field within a region of interest is a method that presents flow using a color palette that typically renders higher velocities more brightly than slower ones, and distinguishes between different flow directions (generally toward the transducer or away from it) by using warm (reddish) and cool (bluish) tones. Very slowly moving and stationary regions are not colored, and a "wall filter" threshold is used to set the minimum cutoff velocity. Color Flow Doppler can provide approximate mean flow velocities in the region of interest, but accuracy is limited due to the short acquisition sequences needed to maintain reasonable frame rates.

Color Flow Doppler requires the acquisition of a rapid sequence of identical transmit-receive events, or "ensemble", to detect and quantify motion by various means, essentially looking for correlated differences in arrival time, or phase, of the signal. The pulse repetition frequency (PRF) can be as fast as permitted by the round trip travel time of sound from the transducer to the maximum depth of the image and back again, but is generally adjusted to the minimum permitted to visualize peak blood velocities without aliasing. Typically, an ensemble of between 8 and 16 pulse-echo events is used for each Doppler scan line in the ROI. Choice of transmit beam focus parameters usually leads to Doppler scan lines that are 2 to 3 times broader than those used for echographic imaging. The requirement to transmit an ensemble of pulses in each beam direction generally leads to slower frame rates for Color Flow Doppler than for echographic imaging. Artifacts from slow frame rate can often be more noticeable in Doppler imaging than in grayscale echography because significant changes in flow can occur over a fraction of a cardiac cycle, and even slight probe motion may result in apparent flow over the entire ROI.

Using a small ROI can improve frame rates, but may limit the assessment of flow abnormalities. For example, a Color Flow ROI using 10 Doppler lines and ensembles of 12 pulses requires 120 events, similar to a full frame echographic image.

In general, high quality Doppler imaging is more technically difficult than echographic imaging in great part because backscattering from blood is very weak compared to tissue. Well known fundamental challenges to producing uncluttered and artifact-free Color Flow images include:

- The requirement for highly repeatable transmit pulses, and very low noise and phase jitter in the acquisition hardware.
- Flow signals are often of the same order of magnitude as various sources of noise, but averaging has an adverse impact on frame rate and other motion artifacts.
- The large contrast between the scattering amplitudes of tissue and blood leads to difficulty in discriminating between vessel walls (strong echo) and moving blood (weak echo), even when the velocity contrast is high. In addition, blood flow velocity is often very slow near vessel walls, which often move (pulsate) in synchrony with the cardiac cycle.
- Doppler pulses are typically longer than echographic pulses, and care must be taken to spatially register the flow and echo images which have different resolutions. This is particularly challenging for small blood vessels since the sample volume for Doppler pulses can be larger than the vessel diameter.

BRIEF SUMMARY

Vector Doppler Imaging (VDI) improves on conventional Color Doppler Imaging (CDI) by giving speed and direction of blood flow at each pixel. Multiple angles of Plane Wave Transmissions (PWT) conveniently give projected Doppler measurements over a wide field of view, providing enough angular diversity to identify velocity vectors in a short time window while capturing transitory flow dynamics. In a variant of the method, only a single plane wave angle is required, providing flexible application to situations of imaging deeper tissue. Fast, aliasing-resistant velocity vector estimators for PWT schemes are disclosed.

The VDI imagery is dynamically presented to the user using a novel synthetic particle flow visualization method disclosed herein. The system and methods have been demonstrated by imaging of the carotid artery on a human volunteer with a 5 MHz linear array.

In the present disclosure, two method types are described: a Doppler-based method that exploits multiple angles of plane wave transmissions; and a gradient-based method, which can operate effectively on only a single plane wave angle of transmission (but can incorporate more than one angle if available). In both methods, a PWT measurement model is partitioned into nonlinear and linear components in a way that simplifies vector velocity computation.

In the multi-angle Doppler-based method of vector flow estimation, each pixel's velocity vector predicts the In-Phase/In Quadrature (IQ) measurements at diverse angles of PWT ensembles through a nonlinear model, which are linearized by transforming with conventional CDI processing (clutter filtering and Kasai autocorrelation) to a set of Doppler frequencies. Blood velocity vector estimation then simplifies as the solution to a small linear weighted least squares (WLS) problem, conditioned on a hypothesized measurement bias due to aliasing. Weights derived from CDI autocorrelation lag variances account for clutter filtering effects. The nonlinearity of the original problem is thus reduced to a discrete search over a finite number of known aliasing bias vectors. Further, the WLS estimator covariance provides information used to qualify pixels for the presence of blood flow.

In the gradient-based vector blood flow estimation method, PW transmission and reconstruction generate a blood motion image sequence in the B-mode flow (B-Flow) modality, at frame rates in the Doppler Pulse Repetition Frequency (PRF) regimen. Pixel ensembles of the IQ data in the image sequence at pixel point p=[x,z] and PRI t are comprised of IQ magnitude values, computed from the IQ data at each pixel p after wall filtering the ensemble. The sequence of values thus captures motion at a frame rate equal to the PRF, revealing fine-scale flow dynamics as a moving texture in the blood reflectivity. Using the chain rule, spatial and temporal derivatives resulting from the space-time gradient of the image sequence couple to the texture flow velocity vector field $[v_x(x,z,t), v_z(x,z,t)]$ at each pixel p and PRI t. The resulting estimation equations are solved by least squares in the Gauss-Markov model context to give the vector flow velocity estimates, which are formulated in the model to be constant over the estimation window.

The gradient-based method allows augmentation of the observation in the estimation model, with conjugate-lag product samples (autocorrelation summands)—in addition to the zero lag (IQ magnitude case)—at lags of higher numbers, and as well as instantaneous Doppler-derived velocity estimates. This augmentation provides improved precision with a trade-off against accuracy.

Compared to the multi-angle Doppler-based process disclosed within, the gradient-based approach allows for a longer time interval for wall filtering, as the acquisition frame does not require partitioning into separate segments for different plane wave transmission angles. Longer wall filter impulse responses with steeper transition bands are then possible, for equivalent capture window times. This allows flexibility in balancing frame rate and sensitivity, and enables application to vector flow imaging of deep tissue where achieving plane wave angle diversity becomes difficult at high frame rates.

To visualize the resulting velocity vector images, a novel technique is disclosed that synthesizes a moving field of points representing particles entrained in the fluid. In its creation, each particle is probabilistically generated at a pixel where flow is detected, and imbued with motion proportional to the velocity vector estimate, scaled down so the viewer may easily perceive motion. Particles migrate across the image from frame to frame under conservation rules that control particle density to the user's preference. The particle motion overlays the detected flow regions, which are color-coded for velocity magnitude.

Using a Philips L7-4 transducer and a Verasonics acquisition system, in vivo VDI on a carotid artery is demonstrated with Doppler-based and gradient-based methods. PWT ensembles collected at seven angles are processed with the Doppler-based VDI process, in a GPU implementation that accommodates the collection rate of 30 fps. A single PWT angle is used to demonstrate the gradient-based process, at a data collection rate of approximately 60 FPS. Video display reveals dynamics of the flow field and shows good detection of flow during diastole. This vector velocity imaging framework demonstrates acquisition frame rates sufficient to capture flow dynamics in the carotid artery. The gradient-based VDI process method is also evaluated for accuracy and precision using a Doppler string phantom.

The particle flow visualization technique is demonstrated to be subjectively informative in conditions of plug, laminar, and turbulent flow.

Note that throughout this disclosure, the terms "Vector Flow", "Vector Velocity", and "Vector Doppler" are used synonymously.

BRIEF DESCRIPTION OF THE SEVERAL VIEWS OF THE DRAWINGS

The foregoing and other features and advantages of the present invention will be more readily appreciated as the same become better understood from the following detailed description when taken in conjunction with the accompanying drawings, wherein.

DETAILED DESCRIPTION

Figure 1:
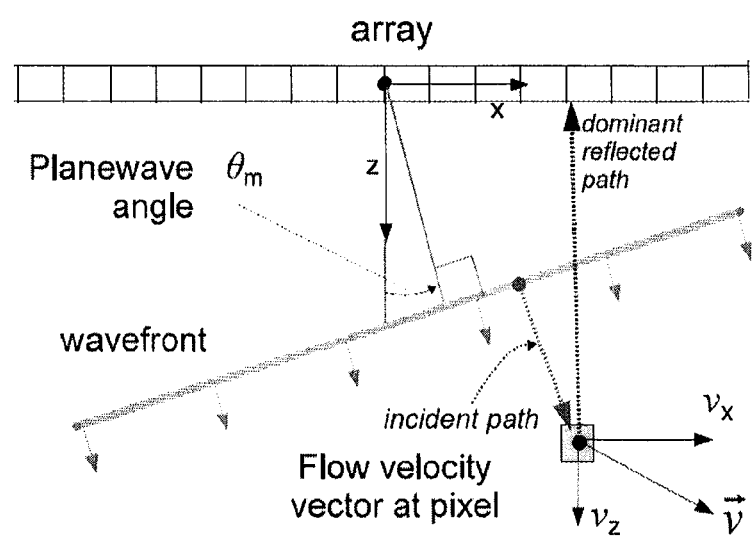
FIG. 1 is an illustration of geometry definitions for a multi-angle plane wave acquisition scheme in accordance with the present disclosure.

In the multi-angle Doppler-based method of vector flow estimation, a PWT measurement model is partitioned into nonlinear and linear components in a way that simplifies vector velocity computation. Each pixel's velocity vector predicts the IQ measurements at diverse angles of PWT ensembles through a nonlinear model, which we linearize by transforming with conventional CDI processing (clutter filtering and Kasai autocorrelation) to a set of Doppler frequencies. Velocity vector estimation then simplifies as the solution to a small linear weighted least squares (WLS) problem, conditioned on a hypothesized measurement bias due to aliasing. Weights derived from CDI autocorrelation lag variances account for clutter filtering effects. The nonlinearity of the original problem is thus reduced to a discrete search over a finite number of known aliasing bias vectors. Further, the WLS estimator covariance provides information used to qualify pixels.

In the gradient-based vector blood flow estimation method, PW transmission and reconstruction generate a blood motion image sequence in the B-mode flow (B-Flow) modality, at frame rates in the Doppler PRF regimen. Pixel ensembles of the IQ data in the image sequence at pixel point p=[x,z] and PRI t are comprised of IQ magnitude values, computed from the IQ data at each pixel p after wall filtering the ensemble. The sequence of values thus captures motion at a frame rate equal to the PRF, revealing fine-scale flow dynamics as a moving texture in the blood reflectivity. Using the chain rule, spatial and temporal derivatives resulting from the space-time gradient of the image sequence couple to the texture flow velocity vector field $[v_x(x,z,t), v_z(x,z,t)]$ at each pixel p and PRI t. The resulting estimation equations are solved by least squares in the Gauss-Markov model context to give the vector flow velocity estimates, which are formulated in the model to be constant over the estimation window.

To visualize the resulting velocity vector image, a novel technique is used that synthesizes a moving field of points representing particles entrained in the fluid. In its creation, each particle is probabilistically generated at a pixel where flow is detected, and imbued with motion proportional to the velocity vector estimate, scaled down so the viewer may easily perceive motion in a "real-time slow-motion" presentation. Particles migrate across the image from frame to frame under conservation rules that control particle density to the user's preference. The particle motion overlays the detected flow regions, which are color-coded for velocity magnitude. Methods for displaying blood flow vector velocity imagery as quantitative velocity spectrum and as vessel flow rate are also disclosed.

Using for example a Philips L7-4 transducer and a Verasonics acquisition system, the present disclosure demonstrates in vivo VDI on neck vasculature. PWT ensembles collected at seven angles are processed with the multi-angle Doppler-based VDI process, in a GPU implementation that accommodates the collection rate of 30 fps. Video display reveals dynamics of the flow field and shows good detection of flow during diastole. This vector velocity imaging framework demonstrates acquisition frame rates sufficient to capture flow dynamics in the carotid artery. The process is conceptually simple and computationally efficient, and it leverages standard CDI processing as its front-end. A single PWT angle is used to demonstrate the gradient-based VDI process at a data collection rate of approximately 60 FPS. The gradient-based VDI process method is also evaluated for accuracy and precision using a Doppler string phantom.

It is to be understood that the angle of the plane wave is measured with respect to a normal at the face of the transducer as shown in FIG. 1 as the angle between the plane wave wavefront and the transducer array.

The particle flow visualization technique is subjectively informative in conditions of plug, laminar, and turbulent flow.

Frame-rate Analysis: Here the benefit to frame-rate, of using the multi-angle Doppler-based blood flow velocity vector computation method, is compared to a conventional rayline-based imaging system. Assume the ensemble length is 18 PRIs, and the PRF is 4 KHz. Then, for seven plane wave angles, the framerate (not including B-Mode acquisitions) of the disclosed method is 32 fps. Comparing this to a steered linear array acquisition approach, with 2:1 multiline acquisitions with 30 transmit lines per frame, giving a framerate of one fps, 32 times slower.

TABLE I

| GLOSSARY | |
|---|---|
| t | PRI index |
| $\theta_m$ | plane wave (PW) transmission angle |

TABLE I-continued

GLOSSARY

| | |
|---|---|
| m | PW angle index |
| M | Number of PW transmission angles per frame |
| N | Number of PRIs for each $\theta_m$ |
| $r_m(t)$ | image point IQ sample |
| $s_m(t)$ | flow signal at PRI t and angle $\theta_m$ |
| H | clutter filter matrix |
| clutter | wall & stationary tissue signal |
| noise | receiver noise of variance $\sigma_n^2$ |
| $\hat{f}_m$ | Doppler frequency estimates at angle $\theta_m$ |
| $\sigma_f^2$ | variance of Doppler frequency estimates |
| $\bar{a}_m$ | lag-1 autocorrelation of flow estimate |
| $a_m(t)$ | t-th conjugate lag-1 flow signal product |

Multi-Angle Doppler-Based Method for Vector Velocity Blood Flow Estimation: Process Description A vector Doppler estimation process in accordance with the present disclosure produces velocity vector estimates for each reconstructed image point. The acquisition scheme ensonifies the tissue with plane wave transmissions, emitted from the array at different plane wave propagation angles. Each plane wave angle is used for several PRIs, so that an ensemble of transmissions is collected at each angle.

Application of Blood Flow Velocity Vector Estimation Method to Wide-Beam Transmissions:

While the methods for generating blood flow velocity vector estimates disclosed here are developed in the context of plane wave transmissions, the methods are equally suitable to multiple wide-beam transmissions, by modifying the bistatic range-rate models accordingly for the wavefront orientation at each pixel.

The estimation process splits computation into three stages. First, Doppler estimation is applied separately to ensemble data collected at each of the transmitted plane wave angles. This is conventional color flow processing that removes stationary tissue effects and produces estimates of Doppler frequency due to projected (relative) blood flow velocity measured at each plane wave angle. Autocorrelation lags and derived statistics, in the manner of the Kasai autocorrelation-based blood Doppler estimation, are a computed byproduct at each image point. The result is a multi-angle set of relative Doppler estimates.

In the second step, the estimate from the first stage in set are combined through a nonlinear least-squares estimation procedure, producing the vector velocity components of blood flow at each image point.

Finally, the third step qualifies the vector velocity estimate at each image point by testing for the presence of flow.

A. Acquisition and Reconstructed Signal Model

The velocity vector estimation procedure is built on an acquisition scheme that transmits plane wave (PW) signals over a set of angles $\theta_m$, for $m \in \{1, \ldots, M\}$. It is assumed that the set of PW angles is symmetric about the normal vector of the array (in the case of curved arrays, located at the array center). Each angle $\theta_m$ defines the direction of travel normal to the wavefront. Acquisitions dwell at each angle for N successive pulse repetition intervals (PRI) at a rate of PRF Hz, forming an ensemble for the angle. In addition, two dummy pulses are transmitted at the beginning of each ensemble to induce a steady state acoustic environment. The acquisition geometry is illustrated below in FIG. 1.

Each acquisition event produces a collection of RF data, from which a two dimensional image is reconstructed by a conventional beamforming process (not described here). Thus for M×N acquisitions, M×N associated images are produced, each with identical spatial sampling coordinates in depth and azimuth. The estimation process processes all data at a given image point identically to, and independently from, the data at other image points. To simplify notation we omit the spatial sampling index in notation throughout Section II.

The signal model describes each beamformed (or otherwise reconstructed) image point signal $r_m(t)$ as the sum of clutter from slow-moving tissue scattering, the blood flow signal $s_m(t)$, and additive white noise with variance $\sigma_n^2$. The model for the observation of the IQ image point of interest, at PRI t and PW angle $\theta_m$ is then $$r_m(t) = s_m(t) + \text{clutter} + \text{noise} \tag{1}$$

for $t = 0, \ldots, N-1$. Collecting the N samples of $r_m$ gives an ensemble of observations in the vector form $$r_m = [r_m(0), \ldots, r_m(N-1)]^T. \tag{2}$$

B. Doppler Estimation at Each Plane Wave Angle

Prior to estimating flow signal parameters, a high-pass filtering matrix H (stationary tissue or "wall" filter) applied to each image point IQ ensemble suppresses the low-Doppler clutter signal. The filter H may be specified by a variety of design techniques, such as polynomial- or sinusoidal-basis regression, or computed on-line by a suitable adaptive method. Applying the filter to the IQ ensemble data gives the signal estimate $$\hat{s}_m = H r_m. \tag{3}$$

Then, applying the Kasai autocorrelation-based blood Doppler method gives mean frequency estimates $\hat{f}_m$ for the flow signal at each PW angle. This step also estimates the flow variance, which the vector estimation process later uses (Section II-C). The Kasai method computes the first autocorrelation lag of the flow signal estimate $\hat{s}_m$ as $$\bar{a}_m = \sum_{t=1}^{N-1} a_m(t) \tag{4}$$

where the individual first-order lagged products $a_m(t)$ are defined as:

$$a_m(t) = \hat{s}_m(t)\hat{s}_m^*(t-1). \tag{5}$$

The mean Doppler frequency $f_m$ induced at angle $\theta_m$ for the image point is then estimated as:

$$\hat{f}_m = \frac{PRF}{2\pi}\tan^{-1}(\bar{a}_m) \tag{6}$$

where $\tan^{-1}$ is the four-quadrant complex arctangent with range $(-\pi, \pi)$, and $\lambda = c/F_c$ is the transmitted pulse's carrier wavelength. It is assumed the $\hat{f}_m$ have estimation error uncorrelated among m, and denote its variance $$\sigma_{\hat{f}_m}^2 = \text{var}[f_m]. \tag{7}$$

The velocity vector estimator described in Section II-C exploits $\sigma_{\hat{f}_m}^2$. This computation (shown in Section C2) requires the ratio $$DSNR_m = [\bar{a}_m]^2 / \sigma_{a_m}^2, \tag{8}$$

which we denote "Doppler SNR" for PW angle $\theta_m$. To this end, the lag variance $\sigma_{a_m}^2$ is estimated as $$\sigma_{a_m}^2 = \frac{1}{N-1} \sum_{t=1}^{N-1} |a_m(t) - \bar{a}_m|^2 \qquad (9)$$

C. Velocity Vector Estimation by Doppler Estimate Combining

Using each image point's set of Doppler frequency estimates and computed statistics at each of the MPW ensemble angles, a combining process produces the desired velocity vector. A bistatic range-rate model relates the per-angle Doppler frequencies estimates to velocity. This linear mapping expresses frequencies as functions of the velocity vector components, corrupted by additive stochastic error and a discrete-valued deterministic bias term due to aliasing of the Doppler frequencies.

This model formulation is linear in the flow velocity vector (the parameter of interest), but non-linear in the set of binary nuisance parameters representing aliasing errors in the Doppler frequency vector b. The approach of the present disclosure is to whiten the model to balance the $\sigma_{f_m}^2$, partition it into its linear and nonlinear components, then invert the linear portion by direct solution while hypothesizing bias vectors through a discrete search. Choosing the lowest residual sum-of-squares (RSS) then identifies the least-square velocity vector estimate. In Section C3 a geometric argument is developed that reduces the size of the discrete search for aliasing bias, and reducing overfitting to noise-only data, by constraining aliasing to be in ensembles of adjacent plane wave angles. Identification of aliasing bias is important to the method, as not accounting for it will cause "blackout" areas in vessel imagery during high-Doppler events. This is because the aliasing bias causes a poor fit in the bistatic range-rate model, and subsequently the WLS solution for the model will consider the event to be noise. Thus, lack of blackouts during, for example, a systole event, indicates the use of aliasing correction. Lack of excessive noise detection at non-flow events indicates constraint of aliasing correction to adjacent plane wave angles.

In contrast, direct IQ-domain or autocorrelation-domain measurement models with least-squares objective functions have velocity related to frequency in a non-linear fashion. This would lead to a two-dimensional non-linear minimization problem, requiring a search for both the magnitude and direction of the flow velocity vector. In the case of narrow-band "plug" flow with high SNR, such an objective function can be sharply peaked with multiple extrema, requiring a fine search and therefore a high computation cost. In our proposed method, the direct solver component circumvents this difficulty and the search is one-dimensional with a discrete, well defined enumeration.

1) Bistatic Range-Rate Model:

It is assumed that the flow signal $s_m(t)$ acquired at PW angle $\theta_m$ is subject to mean Doppler shift dominated by the bistatic range-rate model of acoustic signal processing theory. Here the instantaneous acoustic propagation path includes the projection of the image point's motion vector onto the direction vector for the incident PW transmission angle $\theta_m$ and the reflected wave's return path directly to the closest point of the transducer array (FIG. 1). Collecting the estimated Doppler frequencies into a length-M vector $[\hat{f}_1, \ldots, \hat{f}_M]_T$ (and reserving the notation "^" on f for its multi-angle LS fit in the sequel), the model can be written as:

$$f = Av + b + e, \qquad (10)$$

where the flow velocity vector at the image point is $v = [v_x, v_z]_T$ b represents bias due to aliasing, e is stochastic error, and the model matrix A is dimensioned [M×2] and has rows $a_m(\theta_m)$, where:

$$a_m = \frac{1}{\lambda}[\sin(\theta_m), 1 + \cos(\theta_m)]. \qquad (11)$$

Note that A is determined by the PW angles and can be pre-computed if these are fixed.

Figure 2:
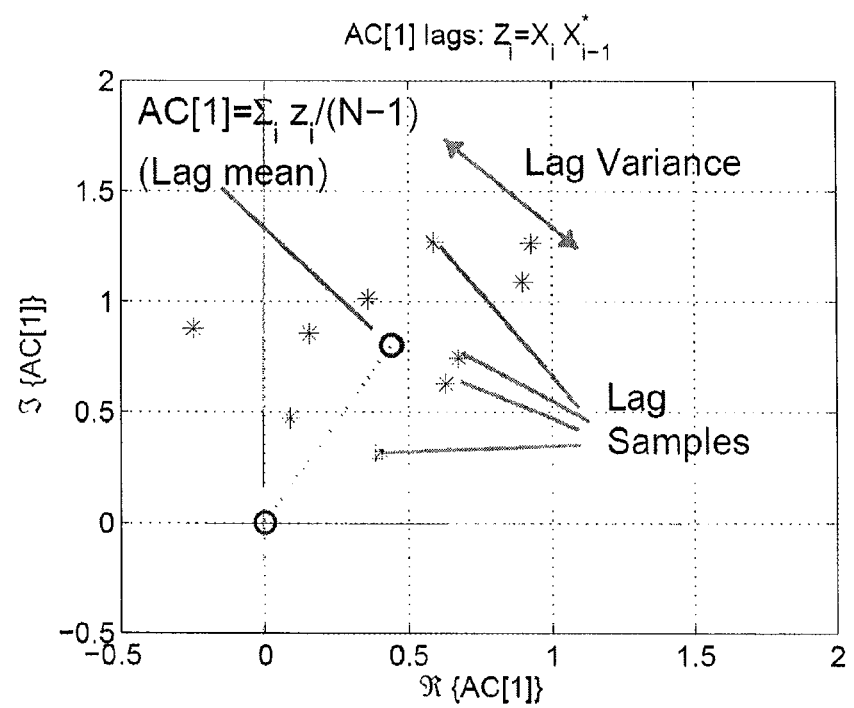
FIG. 2 is an illustration of an example autocorrelation lag-one variance in relation to autocorrelation value magnitude.
Figure 3:
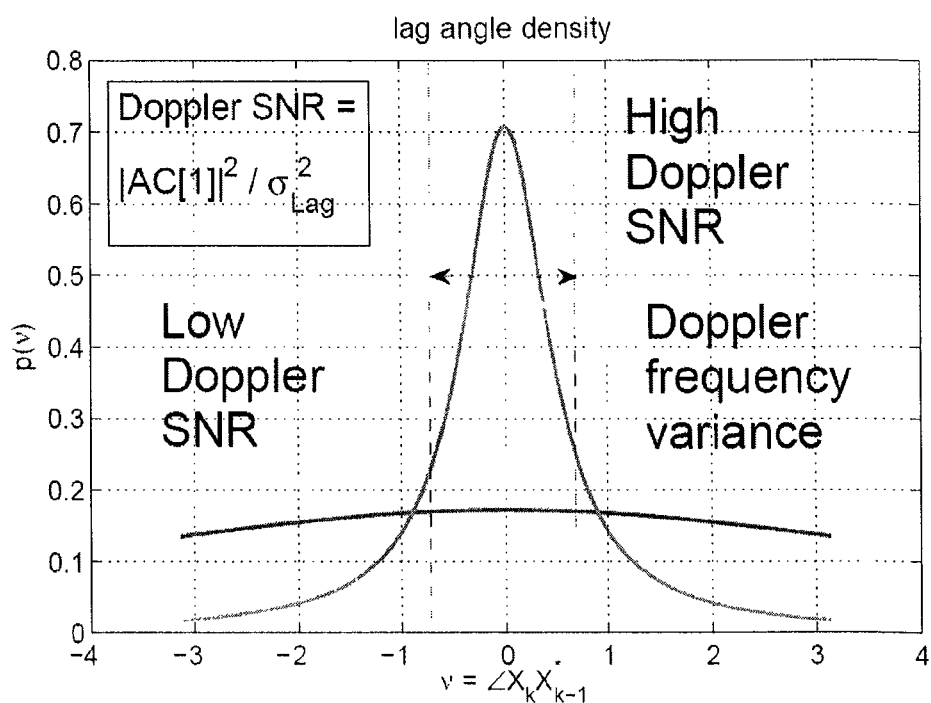
FIG. 3 is an illustration of an example autocorrelation lag-one angle distribution as a function of DSNR.

2) Doppler Frequency Estimate Variance:

The variance $\sigma_{f_m}^2$ (7) of the frequency estimates depends on $DSNR_m$ in (8) and is computed from an empirically-determined mapping that is a rational polynomial approximation. The motivation behind this is in analogy to the variance of the angle associated with a complex Rice random variable. Referring to FIG. 2, it is apparent that as the quantity $DSNR_m$ vanishes, the angle (frequency) becomes more uncertain. In the limit the angle becomes distributed uniformly over $[0,\pi]$, as illustrated in FIG. 3. In practice this effect is more severe on low-Doppler flow interrogated by plane waves arriving at an angle near-broadside to the flow direction, and thus depends also on wall filter characteristics. The mapping from $DSNR_m$ to $\sigma_{f_m}^2$ is shown in graphically in FIG. 4 for the case of 12-pulse ensembles, at a nominal Doppler flow frequency of 0.25*PRF. Although the approximation diverges at high SNR, typical values for regularizing the frequency standard deviation restrict it to be not less than 0.03. This has the good side effect of avoiding the divergent approximation region.

Figure 4:
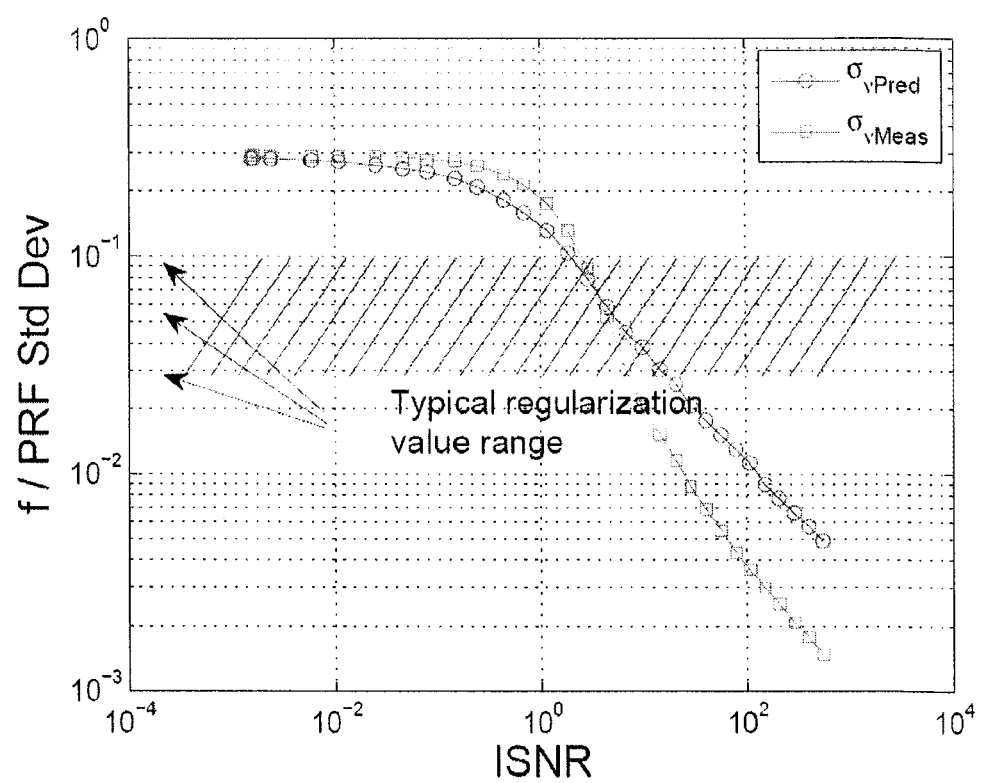
FIG. 4 is a graphical illustration of mapping from $DSNR_m$ to $\sigma_{f_m}^2$.

Defining $\hat{\theta} = \hat{f}/PRF$, the rational polynomial approximation shown in FIG. 4 is described in the MatLab code below. An alternate novel method of computing the frequency standard deviation is presented in the later section disclosing the gradient-based vector flow estimation process.

```
function [varTheta] = dsnr2fvarmap(snr,varargin);
%ricemoments: compute moments of rice R.V. (approximate)
%usage:
% varTheta = var(angle(z)), in rad. squared
% for z = complex gaussian, SNR = |mean(z) | ^2/var(z)
%.
%Verasonics
% jaf 20jul2009
Kvai = length(varargin);kvai = 1; %use kvai and template below:
sizeSNR=size(snr);
%allowed SNR range
snrdbMax=100;
snrdbMin]= -30 ;
SNRRANGE = snrdbMax - snrdbMin;
snrdb = 10*log10(snr(:)');
snrBounded = fdim(snrdb, snrdbMin);
snrBounded = min( snrBounded , snrdbMax - snrdbMin );
Alpha=16;
%pade ratpoly coeffs:
B3= 1.72e+003;
A= [1 56.5685 1600];
snroffsetdb = 6.0;
f = snrBounded - snroffsetdb;
f2 = f. ^2;
denomR = A(3) - A(1)*f2;
denomIminus = A(2)*f ;
denomMag2 = denomR. ^2 + denomIminus. ^2;
Hmag2 = (B3. ^2)./denomMag2;
varTheta = Hmag2. ^ (Alpha/2);
varTheta = reshape(varTheta,sizeSNR);
```

```
end %%%%%%%%%%%%%%%%%%%%%%%%%%%%%%%%%%%%%
function z=fdim(x,y);
%fdim: C99 fdim( ) function emulation.
z=x-y;
z(find(z<0))=0;
end %main
```

3) Hypothesized Aliasing Biases:

In Eqn. 10, elements $b_m$ of the vector b account for aliasing errors, which we model as deterministic and hence as a bias. Here we use a heuristic geometric argument to reduce the size of a naively-constructed search over $2^M$ choices, down to $1+MN_A$ choices, where $N_A$ is the maximum number of PW angles experiencing aliasing. Under a binary hypotheses set $$H_0: |f_m|<PRF/2 \quad (12)$$

$$H_A: PRF>|f_m|<PRF/2 \quad (13)$$

the single-wrap aliasing condition $H_A$ relates the estimated frequency to the un-aliased Doppler frequency, in the noise-free case, as $$H_A: \hat{f}_m = f_m - \text{sign}(\hat{f}_m)PRF. \quad (14)$$

Constructing a bias vector b from any possible binary aliasing configurations gives $2^m$ possible bias vectors. To reduce the size of the feasible set, we note that aliasing is likely to be grouped in adjacent PW angles. Consider a PW transmission angle, say $\theta_F$, that is closest in propagation angle to the true direction of flow at the image point. If aliasing is present at a $\theta_F$, it will be greater than aliasing at any other PW angle, because $\theta_F$ is the angle with greatest range-rate with respect to the PW direction. Thus, the aliasing error will decrease monotonically with the divergence of PW angles relative to $\theta_F$, to some angle of minimum aliasing error. Given a number of acquisition angles affected by aliasing of at most PRF Hz, we reason they must be adjacent in angle.

Flow perpendicular to the array presents a special case: the extreme angles might both experience the same aliasing error magnitude. Defining the PW angle adjacency on a circular format, so the two extreme angles are considered adjacent, addresses this special case as well.

Under the geometric restrictions outlined above, the set of bias vectors are enumerated as follows. In the no-aliasing case $H_0$, b is the zero vector. Aliasing on a single PW angle among M implies M possible bias vectors b. In these cases the bias vectors contain zeroes as elements except at one element among M, where the m-th element representing aliasing bias is set to $$b_m = -\text{sign}(\hat{f}_m)PRF. \quad (15)$$

Generalizing this to two adjacent aliasing angles gives an additional M cases, including the case grouping the two extreme angles. Thus the case of two or fewer aliasing angles gives 2M+1 bias vectors. Extending the hypothesis set by an additional adjacent aliased angle results in another set of M choices. Induction gives the number of hypotheses $N_H$ for $N_A$ or fewer aliased angles as $$N_H = N_A M + 1. \quad (16)$$

For example, assuming up to three simultaneously aliasing PW angles in a seven-angle acquisition scheme, the feasible set of aliasing bias error vectors has 22 distinct vectors. This is illustrated as follows:

The trivial case is that with no aliasing.

In the case of aliasing in a single angle of PW transmission, the columns of expression 17 enumerate all bias vectors for exactly one aliased acquisition angles, out of seven acquisitions ordered by PW angle.

$$\begin{matrix} b_1 & 0 & 0 & 0 & 0 & 0 & 0 \\ 0 & b_2 & 0 & 0 & 0 & 0 & 0 \\ 0 & 0 & b_3 & 0 & 0 & 0 & 0 \\ 0 & 0 & 0 & b_4 & 0 & 0 & 0 \\ 0 & 0 & 0 & 0 & b_5 & 0 & 0 \\ 0 & 0 & 0 & 0 & 0 & b_6 & 0 \\ 0 & 0 & 0 & 0 & 0 & 0 & b_7 \end{matrix} \quad (17)$$

In the case of aliasing in two angles of PW transmission, the columns of expression 18 enumerate all bias vectors for exactly two aliased acquisition angles, out of seven acquisitions ordered by PW angle.

$$\begin{matrix} b_1 & 0 & 0 & 0 & 0 & 0 & b_1 \\ b_2 & b_2 & 0 & 0 & 0 & 0 & 0 \\ 0 & b_3 & b_3 & 0 & 0 & 0 & 0 \\ 0 & 0 & b_4 & b_4 & 0 & 0 & 0 \\ 0 & 0 & 0 & b_5 & b_5 & 0 & 0 \\ 0 & 0 & 0 & 0 & b_6 & b_6 & 0 \\ 0 & 0 & 0 & 0 & 0 & b_7 & b_7 \end{matrix} \quad (18)$$

In the case of aliasing in three angles of PW transmission, the columns of expression 19 enumerate all bias vectors for exactly three aliased acquisition angles, out of seven acquisitions ordered by PW angle.

$$\begin{matrix} b_1 & 0 & 0 & 0 & 0 & b_1 & b_1 \\ b_2 & b_2 & 0 & 0 & 0 & 0 & b_2 \\ b_3 & b_3 & b_3 & 0 & 0 & 0 & 0 \\ 0 & b_4 & b_4 & b_4 & 0 & 0 & 0 \\ 0 & 0 & b_5 & b_5 & b_5 & 0 & 0 \\ 0 & 0 & 0 & b_6 & b_6 & b_6 & 0 \\ 0 & 0 & 0 & 0 & b_7 & b_7 & b_7 \end{matrix} \quad (19)$$

To complete the hypothesis set for the three-angle example, form the union of (17), (18), (19), and with the zero vector (representing the no-aliasing condition). The total is 22 possible bias vectors.

4) Least-Squares Estimation of the Velocity Vector:

Incorporating the above features of the model permits a weighted least-squares estimator for the flow velocity vector at the image point, where the weights are computed to give the conditioned measurements unity variance.

The non-linear model (10) is partitioned into linear and nonlinear components, so that $$\hat{v} = [A^T W A]^{-1} A^T W(f - b_*) \quad (20)$$

where the weight matrix W has its m-th diagonal element as $$w_{m,m} = (\sigma_{mm}^2 + \sigma_{\hat{f}_m}^2)^{-1}. \tag{21}$$

The off-diagonal elements of W are zero because we assume the noise is independent between acquisitions. The lower bound on frequency precision $\sigma_{mm}$ functions as a regularizer. Typical regularization values restrict it to be not less than (0.03☐PRF), commensurate with expected Doppler resolution. The weighting is necessary because of the presence of the stationary tissue/wall filter H in the processing chain. At large relative angles between flow direction and PW propagation direction, especially for slow-moving flow, the relative Doppler frequency can coincide with the stopband of H. This renders the corresponding Doppler frequency estimate extremely noisy. Quantifying the amount of frequency variation through (7) enables optimal weighting for the least-squares formulation.

The optimal aliasing bias vector $b_*$ in 20 solves the minimization problem $$b_* = \arg\min_{b_j}[f - b_j]^T W^{1/2} P^\perp W^{1/2}[f - b_j] \tag{22}$$

where the projector is computed as $$P^\perp = I - W^{1/2} A [A^T W^T A]^{-1} A^T W^{T/2} \tag{23}$$

D. Post-Processing: Interpolation and Detection

Byproducts of the least-squares estimation procedure provide metrics for detecting flow at the image point. Spatially interpolated versions of velocity estimate precision, normalized velocity, Doppler frequency residuals, autocorrelation residuals, and combined autocorrelation power are applied in independent detection tests.

Spatial Interpolation:

Spatial interpolation doubles the sampling density in the x and z dimensions, retaining the original values of the input samples. Linear nearest-neighbor weighting provides the interpolated points.

Velocity Precision:

Due to the weighting W, the whitened errors in Eqn. 20 are i.i.d. and unit variance. Therefore by least squares theory, the velocity estimate covariance is $$\Sigma_{\hat{v}} = [A^T W A]^{-1} \tag{24}$$

$$\sigma_{v_x}^2 = \Sigma_{\hat{v}}(1,1) \tag{25}$$

$$\sigma_{v_z}^2 = \Sigma_{\hat{v}}(2,2). \tag{26}$$

Velocity precision, in squared distance units, is the total error in the velocity estimate:

$$\sigma_{\hat{v}}^2 = \sigma_{v_x}^2 + \sigma_{v_z}^2. \tag{28}$$

A large value for velocity precision indicates that no reliable flow estimate is available for the image point.

Normalized Velocity Magnitude:

The normalized velocity magnitude $v_{NM}$ is the length of velocity scaled for equal precision in the coordinates:

$$v_{nm}^2 = (v_x/\sigma_{v_x})^2 + (v_z/\sigma_{v_z})^2. \tag{29}$$

The image point is the non-flow if the normalized velocity magnitude $v_{nm}^2$ is below a threshold.

Combined Power:

The combined power metric provides an estimate of power seen be all acquisition angles. This aligns the lag-one autocorrelation values $a_m$ by corresponding elements of the fitted frequency $$\hat{f} = A\hat{v}, \tag{30}$$

and weights them by DSNR so that $$\bar{a}_m^0 = DSNR_m \exp(-2\pi \hat{f}_m / PRF) \bar{a}_m \tag{31}$$

$$\bar{a} = \frac{1}{M} \sum_{m=1}^{M} \bar{a}_m^0. \tag{32}$$

Comparing the computed value to a threshold parameter, the image point is non-flow if the combined power $\bar{\alpha}$ is too weak.

Autocorrelation Residual:

Using the elements of the least squares fitted Doppler frequency vector we weight the lag-one autocorrelation vector components by $DSNR_m$ and align them in the complex plane. The sample standard deviation of the result is denoted as the "autocorrelation RSS", $$RSS_{AC} = \frac{1}{M} \sum_{m=1}^{M} |\bar{a}_n^0 - \bar{a}.|^2 \tag{33}$$

Comparing the computed value to a ceiling parameter, the image point is non-flow if the vector of lag-one autocorrelations, aligned by the fitted Doppler frequencies, is too large.

Whitened Frequency Residual:

The fitted frequency vector residual is the sum of squared fitting errors of the least squares velocity vector estimate:

$$RSS = \|f - \hat{f}\|^2 \tag{34}$$

Qualification Tests:

Threshold or ceiling tests, as shown below, independently combine the spatially interpolated metrics described above to qualify the image point. Any test asserting true will declare the point as "non-flow". All tests must pass to qualify an image point as flow. The values of thresholds and ceilings for the tests are adjusted for each scanhead application according to user preference.

$$\text{test}_1: \sigma_{\hat{v}}^2 > T_{prec} \tag{35}$$

$$\text{test}_2: v_{NM}^2 < C_{vel} \tag{36}$$

$$\text{test}_3: RSS > T_{Fresid} \tag{37}$$

$$\text{test}_4: RSS_{AC} > T_{ACresid} \tag{38}$$

$$\text{test}_5: P_{comb} < C_{pow} \tag{39}$$

Gradient-Based Method for Vector Velocity Blood Flow Estimation

Overview

The blood flow vector velocity imaging process disclosed in the previous section requires multiple angles of plane wave (PW) transmissions to construct a robustly invertible model for vector velocity estimates. This section discloses a set of methods needing only a single plane wave transmission angle, and therefore only a single ensemble. In its simplest form, the proposed vector velocity imaging process uses PW transmission and reconstruction to generate a blood motion image sequence in the B-mode flow (B-Flow) modality at frame rates in the Doppler PRF regimen. Pixel ensembles in the image sequence F (p,t) at point p=[x,z] and pulse t are comprised of IQ magnitude values, computed from the IQ data at each pixel p after wall filtering the ensemble. The sequence of values thus captures motion at a frame rate equal to the PRF, revealing fine-scale flow dynamics as a moving texture in the blood reflectivity.

Using the chain rule, spatial and temporal derivatives resulting from the gradient couple to the texture flow velocity vector field $[v_x(x,z,t), v_z(x,z,t)]$ at each pixel p and PRI t. The resulting estimation equations are solved by least squares in the Gauss-Markov model context to give the vector flow velocity estimates, which are formulated in the model to be constant over the estimation window.

We also evaluate variants that include in the observation, conjugate-lag product samples (autocorrelation summands) at lags 0, 1, . . . , as well as instantaneous Doppler-derived velocity estimates; and incorporating data from multiple plane wave angles. These variants include: (1) Gradient-only vector velocity blood flow estimation method using blood reflectivity intensity; (2) Gradient-based, Doppler-augmented vector velocity blood flow estimation method; (3) Gradient-based vector velocity blood flow estimation method using multiple conjugate-lag products of blood reflectivity; and (4) Gradient-based vector velocity blood flow estimation method using multiple conjugate-lag products of blood reflectivity augmented with Doppler estimates, incorporating data from multiple plane wave transmission angles.

Compared to the multi-angle plane wave process presented in the earlier section, this approach allows for a longer time interval for wall filtering, as the frame is not partitioned into separate segments for different plane wave angles. Longer wall filter impulse responses with steeper transition bands are then possible, for equivalent capture window times. This allows flexibility in balancing frame rate and sensitivity, and suggests application to vector flow imaging of deep tissue where achieving plane wave angle diversity becomes difficult.

A typical approach in the use gradient-only vector flow is to achieve model robustness by spatial averaging, rather than temporal aggregation as in the present disclosure. Thus, the present disclosure maintains spatial resolution that would otherwise be degraded by spatial averaging. A further novel aspect of the present disclosure is that it avoids presummation of the observations on which the gradient is performed, as commonly done, in order to obtain quadratic estimates of variance components required for weighting in the weighted least squares (WLS) solution of the Gauss-Markov model.

Using a Philips L7-4 transducer and a Verasonics™ acquisition system, single-angle PWT vector velocity imaging has been demonstrated on a Doppler string phantom and on a carotid artery. PWT ensembles are collected on boresite angle at a 5 KHz PRF. Performance is evaluated in terms of bias and precision of the vector velocity component estimates, and their direction. The process performance disclosed herein offers utility in applications where imaging depth inhibits effective generation of the PWT angular diversity required by the multi-angle Doppler-based VDI process.

Gradient-Based Vector Flow Estimation Methods Description

The present disclosure considers variants of gradient-based flow vector estimation, which compute velocity vector values at each reconstructed image point. In contrast to the multi-angle Doppler-based vector flow estimation method described in the previous section of this disclosure, the gradient-based vector flow estimation methods can operate effectively at only a single plane wave transmission angle. However, they readily generalize to incorporate a plurality of plane wave transmission angles as well. The gradient-based methods are effective when a limited span of plane wave transmission angles are available, such as in the case when imaging tissue at depths significantly larger than the transducer aperture size. Since fewer angles are required, opportunity for more rapid acquisition is available. This provides an additional advantage when imaging with the vector flow modality during events of rapid blood flow dynamics.

Acquisition Scheme and Preprocessing for Gradient-Based Vector Flow Estimation

The acquisition scheme for the gradient-based vector flow estimation methods is substantially similar to that of the multi-angle Doppler method, except that the number of plane wave transmission angles may be as small as one. The tissue is insonated with PW transmissions at a typical Doppler PRF, emitted from the array at one or more plane wave angles, to form conventional Doppler ensembles for each pixel by PW reconstruction. Two precursor pulses transmitted at each plane wave angle, and not further processed, condition the acoustic environment. The ensemble time window is limited to be no longer than flow stationarity assumptions allow. All process variants first process the reconstructed data with wall filtering to remove stationary tissue clutter from each pixel ensemble r(t), where $$r(t)=s(t)+\text{clutter}+\text{noise} \quad (40)$$

where respectively s represents the blood flow signal and t represents the PRI (time) index, so that in vector form the wall-filtered data for N samples is $$\hat{s}=Hr. \quad (41)$$

After wall filtering, the conjugate-lagged products F(p,t,l) of the vector of time samples s(t), at pixel image point p, of signal data vector § are computed in compressed amplitude format, for one or more lags l-0, l-1, . . . as $$F(p,t,l)=\hat{s}(t)\hat{s}(t-l)^*|\hat{s}(t)\hat{s}(t-l)^*|^{-1/2} \quad (42)$$

Note that the terms $\hat{s}(t)\hat{s}(t-l)^*$ are summands of the sample autocorrelation at lag l. These components will be used by variants of the gradient-based vector flow estimation methods, as described below.

Gradient-Only Vector Flow Estimation

In the gradient-only Vector flow estimation process, use of the Doppler estimates is not necessary. Here, a space-time gradient computes the derivatives of the IQ intensity values from the wall filtered data $\hat{s}(t)$ for each image point p. This gradient-only process can incorporate gradients of ensemble data collected at different plane wave transmission angles, but does not use the actual values of plane wave transmission angles employed. In the case of a single plane wave transmission angle, the input of the gradient computation, say F(p,t), may be interpreted as a kind of B-Flow image sequence of image intensity, where $$F(p,t)=F(p,t,0)=|\hat{s}(t)| \quad (43)$$

at pixel p for all t comprising the ensemble. Note that this is the lag-0 The process is developed as follows. Applying the derivative chain rule, $$\frac{d}{dt}F(p,t) = \frac{\partial F}{\partial x}\frac{dx}{dt} + \frac{\partial F}{\partial z}\frac{dz}{dt}. \quad (44)$$

For convenience define the image time sequence at a single pixel p by the vector $$g = \begin{bmatrix} F(p, t=0) \\ \vdots \\ F(p, t=N-1) \end{bmatrix} \quad (45)$$

and similarly the vectors of associated gradient derivative components over time $g_x$, $g_z$, and $\dot{g}$. Assume the expected blood flow component of the images F is unchanging in time over the acquisition window, other than a constant-velocity rectilinear translation due to the spatial independent variables $x=x_0-v_x t$ and $z=z_0-v_z t$. Then the flow velocity vector $[v_x,v_z]^T$ is constrained by computed gradient quantities through the equation $$y_g = -\dot{g} \quad (46)$$

$$= [g_x \; g_z] \begin{bmatrix} v_x \\ v_z \end{bmatrix} + e_g \quad (47)$$

$$= Av + e_g, \quad (48)$$

where we model the diagonal covariance of error vector $e_g$ as $$\mathrm{cov}(e_g) = I\sigma_g^2 \quad (49)$$

The equations 48 and 49 together with unknown 6y form the Gauss-Markov model with classical solution $$\hat{v} = (AA^T)^{-1} A^T y \quad (50)$$

and $$\sigma_g^2 = y^t P_A^\perp y/(N-2), \quad (51)$$

where the projector is formed by $$P_A^\perp = 1 - A(A^T A)^{-1} A^T, \quad (52)$$

giving the blood flow vector velocity estimates $v_x$ and $v_z$, and variance of the blood flow reflectivity gradient noise $e_g$.

The use of the additive error term $e_g$ is admittedly simplistic, because errors in the gradient due to noise, beamforming clutter, and acceleration will appear also in the columns of A.

Detection

In our evaluation, pixels are detected by thresholds and ceilings of flow power estimates, and B-mode priority settings, as in conventional color Doppler imaging. The velocity estimate predicted precision $$\mathrm{cov}(\hat{v}) = (A^T A)^{-1} \hat{\sigma}_g^2 \quad (53)$$

also provides detection information for pixel qualification, identically to the detection methods described in the previous section of this disclosure on Doppler-based vector flow estimation.

Doppler-Augmented Gradient Vector Flow Estimation

While the estimator for component $v_z$ in 50 exhibits bias comparable to the corresponding, independently-derived Doppler estimate computed from the same data (as discussed in the results section), the empirical precision of both $v_x$ and $v_z$ is significantly worse than the Doppler precision. This suggests augmenting the estimator of equation 50 with information containing the Doppler estimate with the goal of improving the precision of the $v_x$ estimate. In the case of a single plane wave transmission angle of 0 degrees (boresite), this augmentation is achieved by constructing the model $$y_{gd} = \begin{bmatrix} -\dot{g} \\ v_d \end{bmatrix} \quad (54)$$

$$= \begin{bmatrix} g_x & g_z \\ 0 & 1 \end{bmatrix} \begin{bmatrix} v_x \\ v_z \end{bmatrix} + \begin{bmatrix} e_g \\ e_d \end{bmatrix} \quad (55)$$

$$= A_{gd} v + e_{gd}, \quad (56)$$

where vector $v_d$ contains N−1 instantaneous Doppler-derived velocity estimates with expectation $v_z$, and where the diagonal observation error covariance is $$\sum_{gd} = \mathrm{cov}(e_{gd}) = \begin{bmatrix} I\sigma_g^2 & 0 \\ 0 & I\sigma_d^2 \end{bmatrix} \quad (57)$$

To counteract aliasing issues with the elements $v_d(t)$ of $v_d = [v_d(0), \ldots, v_d(N-2)]$, the instantaneous Doppler estimates are computed as angular deviates referenced to their mean value, so that $$v_d(t) = \delta v_d(t) + \bar{v}_d(t), \quad (58)$$

where $\bar{v}_d(t)$ is the Kasai autocorrelation-based blood Doppler frequency estimator $$\bar{v}_d(t) = \frac{\lambda}{4\pi} \arctan \bar{a}(1), \quad (59)$$

with $$\bar{a}(1) = \sum_{k=1}^{x-1} s_u s_{x-1}^1, \quad (60)$$

and where the blood differential axial velocity is $$\delta v_d(t) = \frac{\lambda}{4\pi} \arctan[s_t s_{t-1}^* \bar{a}(1)^*]. \quad (61)$$

The mean-square of the set $\delta v_d(t)$ provides the estimate $\hat{\sigma}_d^2$, $$\hat{\sigma}_d^2 = \frac{1}{N-1} E_{t=1}^{N-1} \delta v_d(C) 2. \quad (62)$$

Note 62 is an alternate method to computing the Doppler variance as disclosed in the Doppler-based multi-angle vector flow estimation method of the earlier section, which may be more robust in certain conditions. This, along with the estimate 51 computed earlier, provide the diagonal weighting $$W = \tau_{gd}^{-1/2} \quad (63)$$

The vector velocity estimates are then computed by weighted least squares in accordance with Gauss-Markov theory, in analogy to 50 through 53 by substitution of A with $W A_{gd}$ and y with $W y_{gd}$, to compute the blood flow vector velocity estimates $v_x$ and $v_z$.

The novel method described above in 56 through 63 is generalized to address non-zero plane wave transmission angle of $\theta_m$, similarly to the bistatic range-rate Doppler model using in the previous section for the multi-angle Doppler-based vector flow estimation method, as disclosed below:

$$y_{gd} = \begin{bmatrix} -\dot{g} \\ v_d \end{bmatrix} \tag{64}$$

$$= \begin{bmatrix} g_x & g_z \\ a_{xm}1 & a_{zm}1 \end{bmatrix} \begin{bmatrix} v_x \\ v_z \end{bmatrix} + \begin{bmatrix} e_g \\ e_d \end{bmatrix} \tag{65}$$

$$= A_{gd}v + e_{gd}, \tag{66}$$

where $a_{xm}=(1/2)\sin(\theta_m)$ and $a_{zm}=(1/2)[1+\cos(\theta_m)]$, in analogy to the section above disclosing the Doppler-based vector flow estimation method. For the non-zero plane wave transmission angle formulation, solution follows again similarly to that for 56, using 50 through 53 by substitution of A with W $A_{gd}$ and y with W $y_{gd}$, to compute the blood flow vector velocity estimates $v_x$ and $v_z$.

Multiple-Lag Gradient-Based Estimation

As an alternate to augmenting the gradient-only method described above, additional observations for the gradient may be generated by concatenating gradients of amplitude-compressed complex lags products $s_t s_{t-l}^*$, at lags l of values 1 ... L. The concatenation improves blood velocity vector estimate precision, compared to the gradient-only method. The resulting vector flow estimation method uses no Doppler information. In certain situations, this method may show better bias performance than the Doppler-augmented methods. The compressed complex lags products $s_t s_{t-l}^*$ are computed at lag values higher than one, so that at time t and lag l, $$r_{t,l} = s_t s_{t-l}^* |s_t s_{t-l}^*|^{-1/2} \tag{67}$$

for several l=1 ... L, resulting in $$y_{ml} = \begin{bmatrix} -\dot{g}_1 \\ \vdots \\ -\dot{g}_L \end{bmatrix} = A_{ml}v + e_{ml} = \begin{bmatrix} g_{x1} & g_{z1} \\ \vdots & \vdots \\ g_{xL} & g_{zL} \end{bmatrix} \begin{bmatrix} v_x \\ v_z \end{bmatrix} + \begin{bmatrix} e_{g1} \\ \vdots \\ e_{gL} \end{bmatrix} \tag{68}$$

which is then solved by least squares in accordance with Gauss-Markov theory, in analogy to 50 through 53 by substitution of A with $A_{ml}$ and y with $y_{ml}$, to compute the blood flow vector velocity estimates $v_x$ and $v_z$.

Gradient-Based, Multi-Lag, Multi-Angle Doppler-Augmented Vector Flow Estimation

Disclosed here is the novel method of estimating blood flow velocity vectors in the general case of multiple-angle plane wave transmissions, using compressed complex lags products $s_t s_{t-l}^*$ at multiple lags l={0, 1, ... }, with augmentation by Doppler estimates. Here, the multiple-lag gradients, for L lags are computed from ensemble data collected at multiple angles $\theta_m$ for m={1 ... M}, and appended with Doppler estimates $v_{dm}$ with elements computed per equation 58 for the m-th transmission angle. The data acquisition is therefore identical to that of the Doppler-base vector flow velocity method disclosed in the earlier section. The collective model is then formed by extending definitions of equations 67 and 68 for distinct plane wave transmission angles $\theta_m$ $$y_{mag} = \begin{bmatrix} -\dot{g}_{11} \\ \vdots \\ -\dot{g}_{L1} \\ v_{d1} \\ ----- \\ \vdots \\ ----- \\ -\dot{g}_{1m} \\ \vdots \\ -\dot{g}_{Lm} \\ v_{dm} \\ ----- \\ \vdots \\ ----- \\ -\dot{g}_{1M} \\ \vdots \\ -\dot{g}_{LM} \\ v_{dM} \end{bmatrix} = \begin{bmatrix} g_{x11} & g_{z11} \\ \vdots & \vdots \\ g_{xL1} & g_{zL1} \\ a_{x1}1 & a_{z1}1 \\ ----- & ----- \\ \vdots & \vdots \\ ----- & ----- \\ g_{x1m} & g_{z1m} \\ \vdots & \vdots \\ g_{xLm} & g_{zLm} \\ a_{xm}1 & a_{zm}1 \\ ----- & ----- \\ \vdots & \vdots \\ ----- & ----- \\ g_{x1M} & g_{z1M} \\ \vdots & \vdots \\ g_{xLM} & g_{zLM} \\ a_{xM}1 & a_{zM}1 \end{bmatrix} \begin{bmatrix} v_x \\ v_z \end{bmatrix} + \begin{bmatrix} e_{g11} \\ \vdots \\ e_{gL1} \\ e_{d1} \\ ----- \\ \vdots \\ ----- \\ e_{g1m} \\ \vdots \\ e_{gLm} \\ e_{dm} \\ ----- \\ \vdots \\ ----- \\ e_{g1M} \\ \vdots \\ e_{gLM} \\ e_{dM} \end{bmatrix} \tag{69}$$

$$= A_{mag}v + e_{mag}, \tag{70}$$

where the diagonal error covariance matrix, with blocks conforming to corresponding subvectors of $y_{mag}$, is $$\Sigma_{mag} = \mathrm{cov}(e_{mag}) \tag{71}$$

$$= \mathrm{diag}[1^T\sigma_{g11}^2, \ldots, 1^T\sigma_{gL1}^2, 1^T\sigma_{d1}^2|, \ldots,$$
$$|1^T\sigma_{g1m}^2, \ldots, 1^T\sigma_{gLm}^2, 1^T\sigma_{dm}^2|, \ldots,$$
$$|1^T\sigma_{g1M}^2, \ldots, 1^T\sigma_{gLM}^2, 1^T\sigma_{dM}^2] \tag{72}$$

where the diag operator constructs a diagonal matrix from a vector argument, and where the (L+1)M variance components $\sigma_{glm}^2$ and $\sigma_{dm}^2$ of 72 are computed respectively as per 51 and 62. With the diagonal weighting $W_{mag} = \Sigma_{mag}^{-1/2}$, the blood flow vector velocity estimates $v_x$ and $v_z$ are then computed by least squares in accordance with Gauss-Markov theory, using 50 through 53 by substitution respectively of A with $W_{mag}A_{mag}$ and y with $W_{mag}y_{mag}$.

Using the novel model structure of 72 and 70, the quantities $\sigma_{glm}^2$ and $\sigma_{dm}^2$ of 72 may be iteratively improved along with the blood flow vector velocity estimates $v_x$ and $v_z$ by straightforward application of the Helmert-type quadratic estimation of variance components, well know in the field of geodetics, thereby improving the precision of the computed $v_x$ and $v_z$.

Performance Testing Results

Performance of the some of the novel gradient-based methods described in the application is compared using a Doppler string phantom, in a test conducted at two angles (−23 degrees and level), at depths of 3.5 to four cm. The string speed was 40 cm/s. Data was collected and reconstructed on a 128-channel VDAS ultrasound data acquisition system manufactured by Verasonics, Inc. The results are shown in Table 1. For the sloped string scenario, the table shows clear improvement in lateral velocity precision by the Doppler-augmented and multiple-lag gradient processes, over the baseline gradient-only vector flow estimation process. This improvement comes at the expense of moderate increase in bias. For reference, performance of the Kasai Doppler estimate of $v_z$ is shown as well.

TABLE 1

String phantom evaluation results in mm/sec, showing bias (B), precision (P), and confidence (C) in 3 standard deviations.

| Process | Inc. eg. | B X | C X | B Z | C Z | P X | C X | P Z | C Z |
|---|---|---|---|---|---|---|---|---|---|
| Grad. only | −23 | −28 | 7 | 24 | 3 | 146 | 7 | 70 | 4 |
| Dopp. | −23 | n/a | n/a | 32 | 1 | n/a | n/a | 10 | 1 |
| Grad. aug. | −23 | −34 | 5 | 31 | 1 | 120 | 6 | 11 | 2 |
| M-lag, L = 8 | −23 | −36 | 7 | 26 | 2 | 112 | 5 | 49 | 2 |
| Grad. only | 0 | −60 | 7 | 1 | 6 | 117 | 18 | 120 | 18 |
| Dopp. | 0 | n/a | n/a | 31 | 1 | n/a | n/a | 9 | 1 |
| Grad. aug. | 0 | −77 | 12 | 1 | 3 | 117 | 17 | 18 | 3 |
| M-lag, L = 4 | 0 | −66 | 6 | 1 | 5 | 84 | 12 | 94 | 12 |

Figure 13:
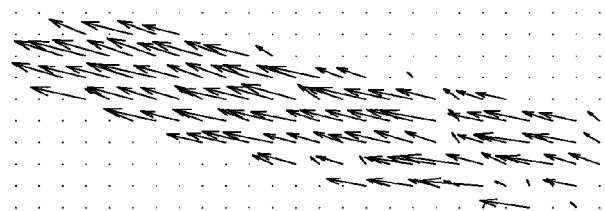
FIG. 13 is an illustration of flow angle estimation by Doppler-augmented gradient approach.

The gradient-based vector Doppler imaging system was also evaluated on a volunteer to image the carotid artery, using a Philips L7-4 linear array transducer. A frame of blood flow vector velocity estimates computed by the Doppler-augmented gradient approach is shown in FIG. 13 in arrow format. Velocity vectors are scaled for viewing. Subjective evaluation of derived in-vivo image video sequences indicates quality comparable to that of the multi-angle Doppler-based vector flow imaging technique disclosed in the earlier section.

Velocity Vector Display by Synthesized Particle Entrainment ("Particle Flow")

The velocity vectors estimated by the method described above will produce vector-valued images, where each pixel has two velocity components. Displaying the magnitude and direction of the vector estimates in two separate image windows can reveal quantitative information through color-bar legends, with the aesthetic appeal of conventional color flow image presentation. However, it has been found that the viewer struggles to perceive dynamic features simultaneously present in two windows on the display screen. A visualization is described below that intuitively conveys dynamic characteristics of the vector pixel information in a single image window.

This method simulates a collection of particles with motion mimicking hypothetical particles entrained in the blood flow. Particle motion is computed for each image frame period, considering estimated velocity vector pixels nearest to the synthesized particle positions. The particles are drawn on the screen inside the detected flow regions, overlaying velocity vector magnitude painted by conventional colorflow velocity display. By this method, flow visualization emerges when the viewer's eye infers entrainment of the particles' motion, as their positions are updated with each new frame. The viewer can arbitrarily scale the motion displayed on the screen to a fraction of actual speed, effectively allowing real-time "slow-motion" inspection of blood dynamics during high-velocity events such as systole in the carotid artery.

A. Visualization Process Overview

In particle flow visualization, a randomly placed set of particles fills all detected flow regions in the image. The particle spatial density is statistically uniform. User preference controls the spatial density of the particles.

At each frame, the set of particles are given motion, by updating their positions according to nearby estimated velocity vectors. The position perturbation is thus the frame time interval multiplied by the velocity vector. If the new particle positions are not located at a pixel representing detected flow, the particle is deemed outgoing, and is deleted from the particle collection.

To check for new incoming particles entering detected flow regions, a similar but contrary position is computed for each flow pixel. Here the negative-time motion of each flow pixel is calculated, using the negated velocity vector estimate. If the backwards motion of the pixel is outside the flow region, new particles are conditionally generated at those pixels. The new "incoming" particles are then appended to the active particle list. The condition for introducing incoming particles adapts to maintain the desired particle density in flow regions, so that incoming and outgoing particles are balanced in consideration of changing flow region size. The overall density condition is enforced by randomly selecting $N_{def}$ of the incoming particles, where $N_{def}$ is the deficit of particles.

B. Visualization Process Description

The steps of the particle flow visualization method are shown in the pseudo-code below:

Step 1: Initialize Particle List: conditionally create particle at each detected flow pixels, with probability equal to density setting D. Compile list of created particles j and their associated positions $[x,z]_j$.

Step 2: Propagation: move each particle in particle list forward in time by advancing its spatial position according to its nearest coincident velocity vector estimate $[\hat{v}_x,\hat{v}_z]$, scaled by desired "slowdown" factor.

Step 3: Test for flow membership: Quantize particle positions to nearest pixels; test new particle quantized positions for flow region membership by evaluating coincident flow detection label; delete particles not in flow from particle list.

Step 4: Back-propagation: move each flow pixels backward in time by negated velocity estimates $[-\hat{v}_x,-\hat{v}_z]$. Quantize positions to nearest pixels.

Step 5: Test back-propagated pixels for flow region membership; if not in a flow pixel, create new particles with probability equal to density setting D.

Step 6: compute particle deficit/surplus;

Step 7: if deficit: generate sufficient number of new particles at random locations in flow to eliminate deficit.

Step 8: if surplus: select random subset of current particle list to delete

Step 9: Draw all detected flow pixels on display frame, with magnitude of velocity vector $v_m^2=\hat{v}_x^2+\hat{v}_z^2$ mapped by desired color map.

Step 10: Draw all particles in current particle list at their associated positions $[x, z]_j$.

Step 11: Next Frame

Figure 5:
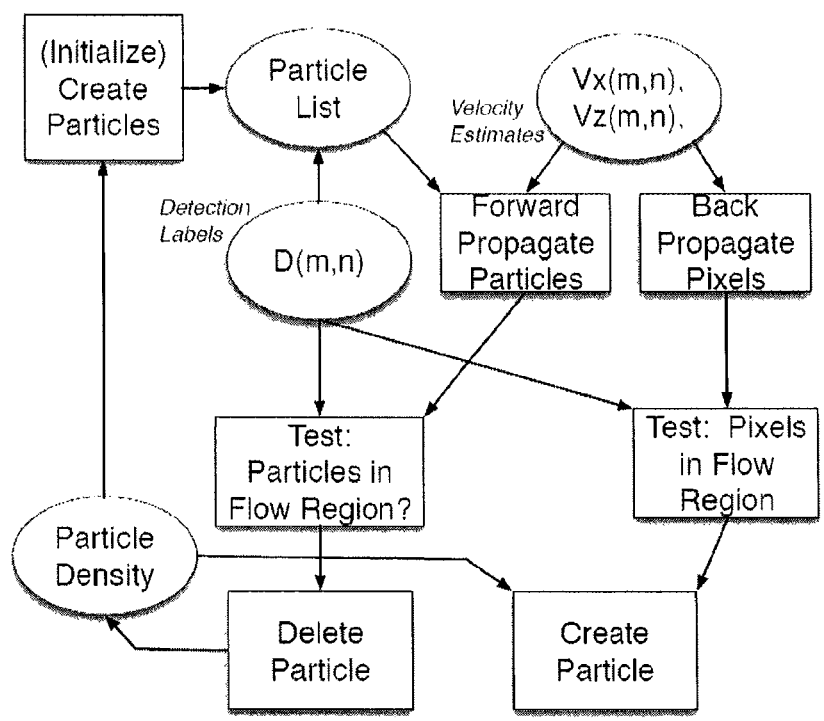
FIG. 5 is a flow diagram showing a relationship between process functions and data components.

FIG. 5 shows the relationship between the process functional and data components.

Figure 7:
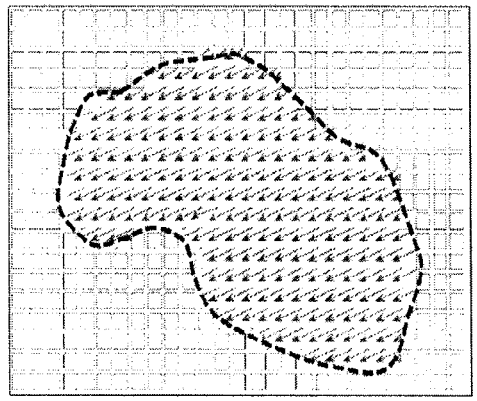
FIG. 7 is an illustration of the main stages of the particle flow visualization process of the present disclosure.
Figure 7:
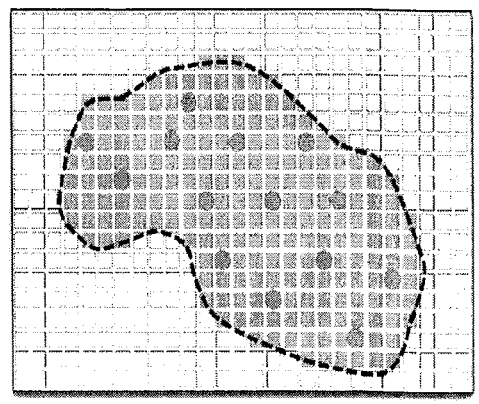
Figure 7:
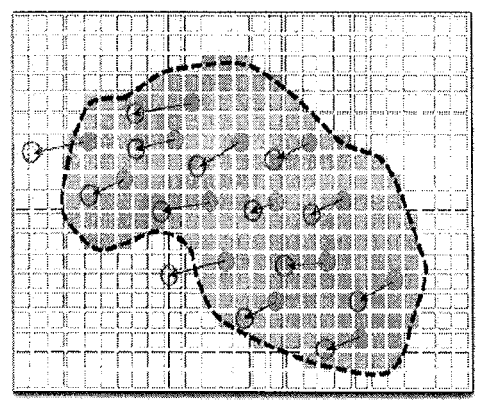
Figure 7:
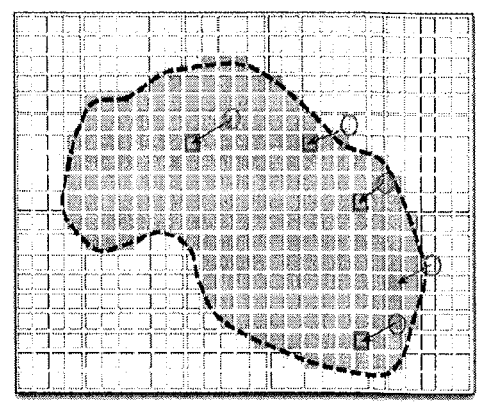

The main stages of the visualization process are illustrated in FIG. 7. Panel A shows a representative flow region with flow pixels labeled in blue arrows.

In Panel B of FIG. 7, the initialization phase defines the particle distribution:

Initialize:
1) User Sets Pixel Density D
2) Collect list of $N_{pix}$ flow pixel locations
3) $N_{part}=D*N_{pix}$
4) Choose $N_{part}$ random subset of flow pixels Panel C of FIG. 7 illustrates the forward propagation step:
Propagate Particle Positions from Frame k to k+1 ($t=t+T_f$)
1) $[x, z]_{k+1}=[x, z]_k+T_f*[v_x, v_z]_k$
2) Quantize particle positions to pixel indices
3) Test if particles in flow pixels; if true then delete particle Panel D of FIG. 7 illustrates the back-propagation step: Back-Propagate Pixel Positions from Frame k to k−1 (t=t−$T_f$)

1) $[x, z]_{k-1} = [x, z]_k - T_f * [v_x, v_z]_k$

2) Quantize pixel positions

Figure 6:
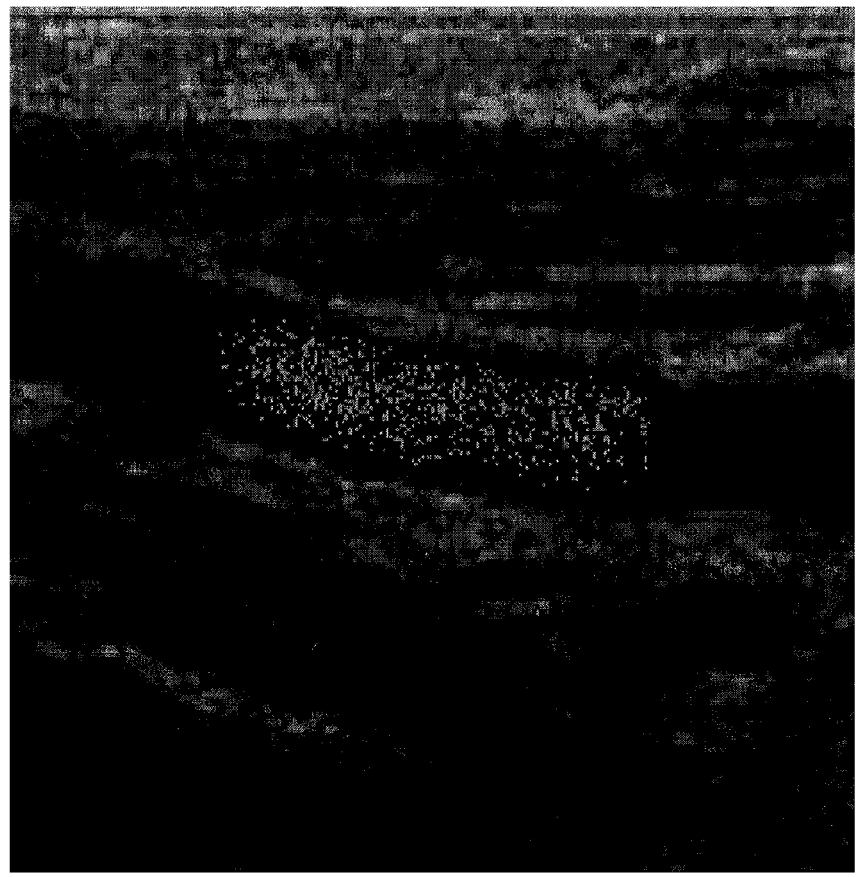
FIG. 6 is an illustration of an example frame of particle flow visualization applied to carotid artery vector flow imaging.

3) Test if pixels out of flow pixels; If true, create new particle at [x, z]k with probability D FIG. 6 shows an example frame of the particle flow display process from a carotid artery scan. Synthesized particles (orange) overlay detected flow regions color-coded by velocity vector magnitude (blue).

C. Visualization Process Implementation

The particle flow visualization process invention is shown below implemented in the MatLab programming language.

```
function [xMotion,yMotion ,trel,iiOut,iiOutIn2D,stateOut ] = ...
    particleFlow6(vx,vy,displayThreshMap,t,flowParams,...
    BmodeSize,TwoD2ColorSamplingRatio,state);
%particleFlow6: display particle flow based on vector velocity map
% Accounts for inflowing particles.
%single history image page, with tests and constant # particles sustained
%signature:
% [xMotion,yMotion ,trel,iiOut,iiOutIn2D ] = particleFlow5( ...
% vx,vy,displayThreshMap,t, flowParams)
% where:
% vx, vy ¯ MxN velocity component map
% displayThreshMap ¯ spatial relative probability map of particle
%    creation
% the folowing are scalar quantities:
% t = time index;
% flowParams - structure with the following members:
%    density,displaySensitivity,Nhist
% TwoD2ColorSamplingRatio - set to 1.0 if
%.
% where:
% density = avg spatial density of new particles
% displaySensitivity = scale to particle creation probability threshold
% Nhist = state history buffer size in frames.
%-
% Outputs:
% xMotion,yMotion : cell arrays of X and Y particle position snapshots in
% trajectory history.
% trel - relative times of history snapshots
% iiOut,iiOutIn2D - "lex" position indices of particels in colorbox, and
% image (if differently sized than colorbox).
% John Flynn 9/28/2010
debugOn =0;
asserts = 1; %set to check for error conditions
nanFix = 1; %set to fix NaNs in vx,xy
persistent debugcounter
persistent Mpart Npart
detIndexCompute = 1;
if nargin<8,
    persistent s
else
    if isempty(state),
        state.s = [ ];
    end
    s = state.s;
end
cboxSize = size(displayThreshMap);
if nargin<6,
    BmodeSize=[ ];
end
if isempty(BmodeSize),
    BmodeSize= cboxSize;
end
if nargin<7,
    TwoD2ColorSamplingRatio=[ ];
end
if isempty(TwoD2ColorSamplingRatio),
    TwoD2ColorSamplingRatio= 1;
end
%assumes cbox cannot be bigger/outside BW
colorboxIsSmaller = ¯isequal(cboxSize,BmodeSize);
if colorboxIsSmaller,
    cboxXOffset = round( ...
        BmodeSize(2)/2 − cboxSize(2)/2*TwoD2ColorSamplingRatio ) ;
else
    cboxXOffset = 0;
end
[M,N]=size(vx);
if ¯isequal([M,N],size(vy)) | ¯isequal([M N],cboxSize),
    [M,N],size(vy)
    [M N],cboxSize
    error('sizes incorrect')
end
if nanFix,
    nind1=find(isnan(vx));
    vx(nind1)=0.0;
    nind2=find(isnan(vy));
    vy(nind2)=0.0;
    if asserts,
        if ¯isempty(nind1) | ¯isempty(nind2)
            disp([mfilename,': condition number excess. '])
        end
    end
end
if asserts,
    foundnans = 0;
    if any(isnan(vx(:)))
        foundnans=foundnans+1;
    end
    if any(isnan(vy(:)))
        foundnans=foundnans+1;
    end
    if any(isnan(Mpart(:)))
        foundnans=foundnans+1;
    end
    if any(isnan(Npart(:)))
        foundnans=foundnans+1;
    end
    if foundnans ¯=0,
        disp([mfilename,':assert:foundnans=',num2str(foundnans)])
        if debugOn>0,
            keyboard
        end
    end
end
%extract params from struct:
density = flowParams.density ;
rejectSensitivity = flowParams.displaySensitivity ;
Nhist = flowParams.Nhist ;
if Nhist ¯= 1, error('only single history Nhist==1 allowed'),end
velocityScale=flowParams.velocityScale;
%find flow locations for this frame:
%subset of x,y positions which are flow:
flowind=find( displayThreshMap ¯=0);%flowlist:
NumFlow = length(flowind);
[Mflow,Nflow]=ind2sub([M N],flowind);
NumParticlesInFrame=round(density*NumFlow);%number of particles used
if isempty(Mpart),
    %init:
    %randomize selection of flow indices
    [¯,tempind]=sort(rand(1,NumFlow));
    %a random selection from flow indices to use as particles.
    tempind=tempind(1:NumParticlesInFrame);
    Mpart=Mflow(tempind);
    Npart=Nflow(tempind);
end
partind =sub2ind([M,N],round(Mpart),round(Npart));
if isempty(partind),
    [xMotion,yMotion,partind,Mpart,Npart,iiOut,iiOutIn2D,trel]=deal([ ]);
    return
end
%current particles: - - - - - - - - - - - - - - -
```

```
%propagate all current particles:
MpartNew = Mpart - velocityScale*vy( (partind(:)));
NpartNew = Npart + velocityScale*vx( (partind(:)));
%quantize positions to indices
iMpartNew = round(MpartNew);
iNpartNew = round(NpartNew);
%check if new positions still in cbox
particlesOut = ...
iMpartNew<1 | iMpartNew>M | iNpartNew<1 | iNpartNew>N ;
outind = find(particlesOut);
%remove particles which are out of cbox, from list:
iMpartNew(outind) = [ ];
iNpartNew(outind) = [ ];
partind(outind) = [ ];
%check if new particles still in flow:
newind =sub2ind([M,N],iMpartNew,iNpartNew);%convert row,col to index
detMap = displayThreshMap(newind);
detind = find(detMap ¯=0); %these in flow regions
missind = find(detMap==0); %these are out of flow regions
%remove particles which are out of flow region,, from list:
iMpartNew(missind) = [ ];
iNpartNew(missind) = [ ];
partind(missind) = [ ];
NumPartRemaining = length(iMpartNew);
NumOutflow = length(outind) + length(missind);
%%%%%%%%%%%%%%%%%%%%%%%%%%%%%%%%%%%%%%%%%%%
%Check for inflow (immigrant) particles: - - - - - - - - - -
%propagate (backwards) all current particles:
% did they come from outside box or flow region?
%need to compute unit-length motion vectors:
vmag=sqrt(vy. ^2 + vx. ^2);
%vmag(vmag==0)=1; %handle zero magnitude case
vyu = vy./vmag ; vxu = vx./vmag ;
%unit-length motion (any motion from adjacent pixels to flow pixels)
%using unit motion to find adjacent pixels in dir of flow
MpartInfluxNewU = Mflow + vyu(flowind);
NpartInfluxNewU = Nflow - vxu(flowind);
%quantize positions to indices
iMpartInfluxNewU = round(MpartInfluxNewU);
iNpartInfluxNewU = round(NpartInfluxNewU);
%check which outside colorbox (therefore inflowing)
particlesInfluxOut = iMpartInfluxNewU<1 | iMpartInfluxNewU>M | ...
    iNpartInfluxNewU<1 | iNpartInfluxNewU>N ;
%need to add original corresponding to these
outIndInflux = find(particlesInfluxOut);
% particles to display
MpartInfluxDisp = Mflow(outIndInflux) ...
    - velocityScale*vy(flowind(outIndInflux));
NpartInfluxDisp = Nflow(outIndInflux) ...
    + velocityScale*vx(flowind(outIndInflux));
partind3A = flowind(outIndInflux);
%these still in colorbox:
%check these for inside flow region
stillinIndInflux = find(¯particlesInfluxOut);
%check which outside flow (therefor inflowing)
newindInflux = sub2ind([M,N], ...
    iMpartInfluxNewU(stillinIndInflux), ...
    iNpartInfluxNewU(stillinIndInflux));%convert row,col to index
detMap = displayThreshMap(newindInflux);
outindFlowInflux = find(detMap==0); %these are out of flow regions, add
% originals to display list
%display/track subset of new candidate inflow particles:
[¯,subsetInd]=sort(rand(1,length(outindFlowInflux)));
NumInflow = min(NumOutflow,round(density*length(outindFlowInflux)));
subsetInd=subsetInd(1:NumInflow);
outindFlowInflux = outindFlowInflux(subsetInd);
outindFlowInfluxSub = stillinIndInflux(outindFlowInflux);
MpartFlowInfluxDisp = Mflow(outindFlowInfluxSub)...
    - velocityScale*vy(flowind(outindFlowInfluxSub));
NpartFlowInfluxDisp = Nflow(outindFlowInfluxSub) ...
    + velocityScale*vx(flowind(outindFlowInfluxSub));
partind3B = flowind(outindFlowInflux);
NnewFromInflow = length(partind3A) + length(partind3B);
%%%%%%%%%%%%%%%%%%%%%%%%%%%%%%%%%%%%%%%%%%%
%replace emigrated particles with newly
%created particles randomly inside flow region:
numToCreate = NumParticlesInFrame - ...
    (NumPartRemaining + NnewFromInflow) ; %account for immigrants
%generate new particles somewhere inside flow region:
[¯,partind2]=sort(rand(1,NumFlow));%randomize selection of flow indices
%a random selection from flow indices to use as particles.
partind2=partind2(1:numToCreate);
Mcreate=Mflow(partind2);
Ncreate=Nflow(partind2);
%unquantized positions:
MpartNew(outind)=[ ];NpartNew(outind)=[ ];
MpartNew(missind)=[ ];NpartNew(missind)=[ ];
%update particle lists
Mpart = clip( ...
    [MpartNew;Mcreate;MpartFlowInfluxDisp;MpartInfluxDisp ],[1 M]);
Npart = clip(...
    [NpartNew;Ncreate;NpartFlowInfluxDisp;NpartInfluxDisp ],[1 N]);
%cull extra particles in mem. (note this is not tracked by iiOut)
maxParticles = round(prod(cboxSize)/2);
NumParticles = length(Mpart);
if NumParticles>maxParticles,
    [¯,thinInd]=sort(rand(1,NumParticles ));
    NumThin = NumParticles-maxParticles;
    thinInd=thinInd(1:NumThin);
    Mpart(thinInd)=[ ];
    Npart(thinInd)=[ ];
End
iiOut = [...
    partind(:); ...
    flowind(partind2(:)); ...
    partind3A; ...
    partind3B(:)];
%outputs:
xMotion = Npart;
yMotion = Mpart;
%
if colorboxIsSmaller,
    [M2,N2] = ind2sub( [M N], iiOut);
    iiOutIn2D ={sub2ind(BmodeSize,M2, N2+ cboxXOffset)};
end
trel=[ ];
end %particle flow synthesis
%%%%%%%%%%%%%%%%%%%%%%%%%%%%%%%%%%%%%%%%%%%
function y = clip(x,bnds);
low =bnds(1);
hi = bnds(2);
y = min(max(x,low),hi);
end %
```

D. Visualization Process Usage and Test

This section gives a MatLab code example of using and testing of the particle flow visualizer invention.

```
function varargout=particleflow_demo;
% particleflow_demo: Demonstrate use and operation of
% the particle flow display algorithm
% "particleflow6.m" for vector doppler data.
%
% Generates simulated vector flow data images and invokes the
% vector flow display invention "particleflow6.m".
%john flynn 10/13/2011
persistent hspat spnoiseind spnoise
Nframes = 4000;
    cmapCFI = grayscaleVDImap;
Mbw= 256;Nbw= 256;
```

-continued

```
bwsize = [Mbw Nbw];
M=Mbw;N = floor(Nbw/2);
cboxsize = [M N];
BW = conv2(rand(Mbw,Nbw),ones(10)/100,'same');
interpFactBW = 1;
%simulate the flow data:
Vxy = .2*kron(exp(2*pi*i*[.13,.8;-.48 , .05]), ones(M/2,N/2));
Vx=real(Vxy);
Vy=imag(Vxy);
Vx = filter(ones(33,1)/33,1,filter(ones(33,1)/33,1,Vx));
Vy = filter(ones(33,1)/33,1,filter(ones(33,1)/33,1,Vy) );
Pac=kron([0 1;1,0],ones(M/2,N/2));
minVelBin = 5;
maxVelColorBin=255;
%
partFlowParam.density = 1/10;
partFlowParam.displaySensitivity = .3;
partFlowParam.Nhist = 1 ;
partFlowParam.velocityScale = 1 ;
for k=1:Nframes,
    Mo2 = round(M/2); No2= round(N/2);
    Pac=zeros(M,N);
    dbox = round(min(M,N)/6*(cos(k/100)*.5+2));
    Pac(Mo2-dbox:Mo2+dbox,No2-dbox:No2+dbox)=1;
    [Xh,Yh, trel,indPart,indPartIN2D ]= ...
        particleFlow6(Vx,Vy,Pac,k,partFlowParam,bwsize,interpFactBW );
    BWk = BW;
    cboxXOffset = round( bwsize(2)/2 - cboxsize(2)/2*interpFactBW ) ;
    detInd = find(Pac ~=0);
    [ ii2, jj2 ] = ind2sub( cboxsize, detInd );
    [iihIn2D2] = sub2ind( bwsize, ii2, jj2+cboxXOffset );
    if ~isempty(iihIn2D2),
        BWk(iihIn2D2) = 128 + 128/2 + minVelBin ;
    end
    BWk(indPartIN2D{1}) = maxVelColorBin;
    image(BWk),colormap (cmapCFI)
    drawnow
end
end %main %%%%%%%%%%%%%%%%%%%%%%%%%%%%%%%%%%%%%%%%%%%%%
function [cmap] = grayscaleVDImap
% Function to create colormap for vector display.
%parse input for alternate map loading
x = [linspace(0,.2,64), ...
    linspace(.2,0,64),linspace(.25,1,128)];
z = [sqrt(linspace(1,.001,128)),...
    linspace(.03,.2,128) ];z(end) = 1;
y = .9*linspace(-1,1,256). ^2;
cfimap01 = [x(:),y(:),z(:)];
dopplerSubMap=cfimap01;
cmap = zeros (256,3);
% load linear greyscale in 1:128
cmap(1:128,1) = (0:(1/127):1)';
cmap(1:128,2) = (0:(1/127):1)';
cmap(1:128,3) = (0:(1/127):1)';
% load color map in 129:256
cmap(129:256,:) = dopplerSubMap(1:2:256,:);
end
```

Display of Measured Blood Flow Properties Derived from Blood Flow Velocity Vectors.

1. Method for Display of Blood Flow Vector Velocity Imagery as the Quantitative Velocity Spectrum The Spectral Doppler method reports the spectrum of flow velocity and how it varies over the cardiac cycle, and it usually presents the spectrum graphically as a spectrogram and audibly through loudspeakers. Moreover, the Spectral Doppler method computes the power spectrum of flow velocity obtained over a sequence of transmissions, and usually presents the spectrum graphically as a spectrogram and audibly through loudspeakers. Access to the full time-varying spectrum of blood velocities allows accurate calculation of mean and peak flow velocities within the sample region and provides the most complete characterization of flow disturbances of all the ultrasound Doppler methods.

One common display function associated with Spectral Doppler is frequency scale correction, to provide quantitative measurements from the computed spectra, thereby producing the blood velocity spectra and spectral trace. Typically the spectral frequency axis is corrected by the cosine of the angle between an estimate of the flow direction, and the direction of the transmitted ensemble used in production of the Doppler spectrum.

Here a method of providing the quantitative blood flow property, the velocity spectrum is disclosed, comprising: using the blood flow velocity vector angle estimates, from pixels coincident to the Spectral Doppler sample volume, as spectral trace frequency axis corrective scale factors, specifically the reciprocal of the bistatic range rate model for the spectral ensemble angle, i.e. $1/[\sin(\_a)\cos(b)+(1+\cos(a))\sin(b)]$, where a is the spectral plane wave transmission angle, and b is the blood flow velocity vector estimated by methods disclosed in the earlier sections. Traditionally, such correction is provided by operator estimation from gross vascular geometry, and ignores fine-scale spatio-temporal features of the true blood flow. In this disclosure, the quantitative measurement of blood velocity spectrum is provided at a time resolution equal to the spectral frame-rate, and at a pixel spatial resolution. The blood velocity spectrum image, thusly scaled, is then displayed analogously to the conventional spectral Doppler image trace format, with the vertical axis labeled in velocity units of distance per unit time.

2. Method for Display of Blood Flow Vector Velocity Imagery as the Quantitative Instantaneous Blood Flow Rate Through a Vessel Blood flow rate through a vessel is measured in units of volume per unit time, e.g. ml/sec. Using the blood flow velocity vector estimates computed over a surface that is a slice of 3D reconstructed voxels bisecting a vessel in the tissue, the area integral of the blood flow velocity vector estimates projected to the normal vectors of their associated slice voxels, where the integration region is taken over the bisecting surface slice, provides a quantitative measure of instantaneous blood flow rate through the vessel. The instantaneous blood flow rate image is then displayed analogously to the conventional spectral Doppler image trace format, with the vertical axis labeled in flow rate units of volume per unit time.

CONCLUSION

The vector Doppler imaging system was tested on a volunteer to image the carotid artery and nearby neck vasculature using a Philips L7-4 linear array transducer.

Figure 8:
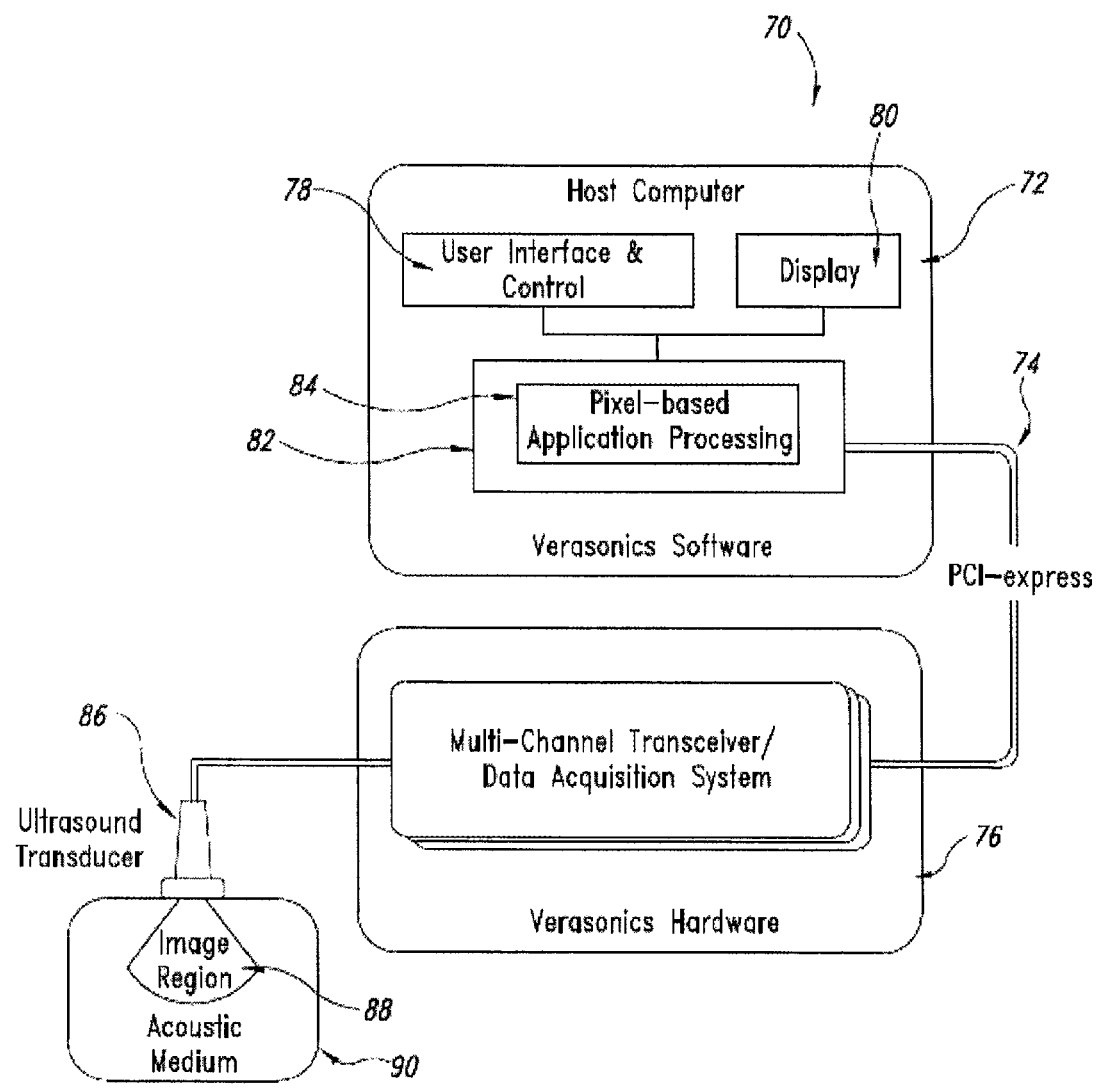
FIG. 8 illustrates a high-level representation of the system architecture for the processes of the present disclosure.

FIG. 8 is a system level block diagram that represents a high-level system architecture 70 for implementing the processes of the present disclosure. It is to be understood that this is merely one representative embodiment, and the illustrated architecture 70 is not a requirement for all embodiments of the present disclosure.

The architecture 70 includes a host computer 72 coupled via a PCI-express 74 to a multi-channel transceiver and data acquisition system 76. The host computer 72 has a user interface and control 78, and a display 80, both coupled to a processor 82 that utilizes the pixel-based application processing software 84. The multi-channel transceiver and data acquisition system 76 hardware are coupled to an ultrasound transducer 86 that is used to image a region 88 in an acoustic medium 90. Because these components are readily commercially available, they will not be described in detail herein.

Pixel Oriented Processing

Figure 9:
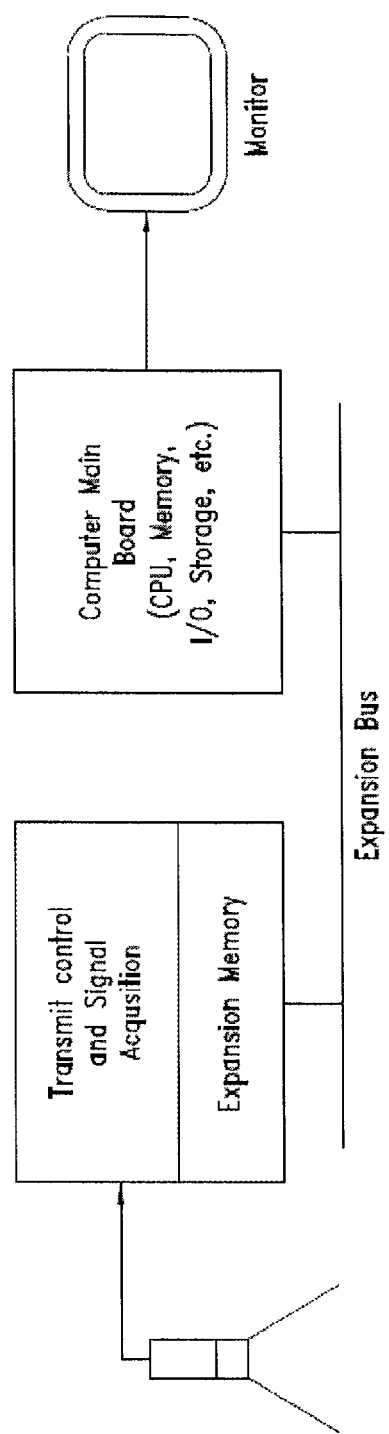
FIG. 9 is a schematic representation of a software-based architecture of one embodiment of pixel-oriented processing.

The software-based method and system architecture in accordance with one embodiment of the present disclosure implements all real-time processing functions in software. The proposed architecture is shown schematically in FIG. 9.

The only custom hardware component in the software-based system is a plug-in module to the expansion bus of the computer that contains the pulse generation and signal acquisition circuitry, and a large block of expansion memory that is used to store signal data. The signal acquisition process consists of amplifying and digitizing the signals returned from each of the transducer elements following a transmit pulse. Typically, the only filtering of the signals prior to digitization, other than the natural band-pass filtering provided by the transducer itself, is low pass, anti-aliasing filtering for A/D conversion. The signals are sampled at a constant rate consistent with the frequencies involved, and the digitized data are stored in memory with minimal processing. The straight-forward design of the signal acquisition allows the circuitry to be implemented with off-the-shelf components in a relatively small amount of board area.

Figure 10:
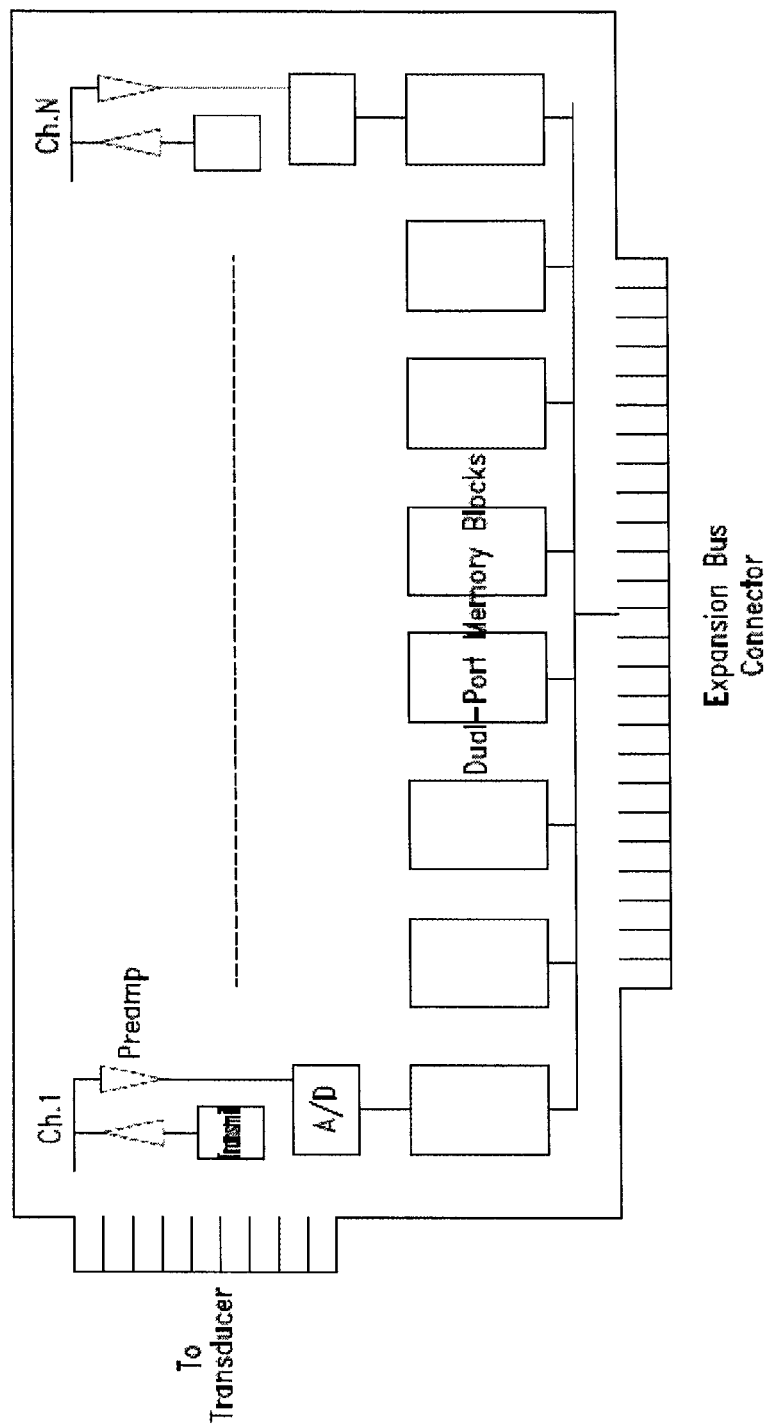
FIG. 10 is a diagram of a plug-in module formed in accordance with the pixel-oriented processing.

A more detailed look at the plug-in module is shown in FIG. 10. Multiple acquisition channels are shown, each composed of a transmitter, receiver pre-amplifier, A/D converter, and memory block. During receive, the transducer signals are digitized and written directly to the individual memory blocks. The memory blocks are dual-ported, meaning they can be read from the computer side at the same time acquisition data is being written from the A/D converter side. The memory blocks appear as normal expansion memory to the system CPU(s). It should be noted that the size of the plug-in module is not limited to the normal size of a standard computer expansion card, since the system is preferably housed in a custom enclosure. Also, multiple plug-in modules can be used to accommodate a large number of transducer elements, with each module processing a subset of the transducer aperture.

The components for the plug-in module, including amplifiers, A/D converters and associated interface circuitry, and the needed components for transmit pulse generation and signal acquisition are readily commercially available components and will not be described in detail herein. The memory block needed for RF data storage of echo signals obtained from received echoes is essentially the same circuitry as found in commercially available plug-in expansion memory cards, with the addition of a second direct memory access port for writing the digitized signal data. (The received echo signal data is generally referred to as RF data, since it consists of high frequency electrical oscillations generated by the transducer.) The memory is mapped into the central processor's address space and can be accessed in a manner similar to other CPU memory located on the computer motherboard. The size of the memory is such that it can accommodate the individual channel receive data for up to 256 or more separate transmit/receive cycles. Since the maximum practical depth of penetration for round trip travel of an ultrasound pulse in the body is about 500 wavelengths, a typical sampling rate of four times the center frequency will require storage of as many as 4000 samples from an individual transducer element. For a sampling accuracy of 16 bits and 128 transducer channels, a maximum depth receive data acquisition will require approximately one megabyte of storage for each transmit/receive event. To store 256 events will therefore require 256 MB of storage, and all totaled, a 128 channel system could be built on a few plug-in cards.

Another aspect of the software-based ultrasound system is the computer motherboard and its associated components. The motherboard for the proposed design should preferably support a multi-processor CPU configuration, for obtaining the needed processing power. A complete multi-processor computer system, complete with power supply, memory, hard disk storage, DVD/CD-RW drive, and monitor is well-known to those skilled in the art, can be readily commercially purchased, and will not be described in greater detail.

A software-based ultrasound system must truly achieve "high-performance," meaning image quality comparable to existing high-end systems, in order to provide a significant benefit to the health care industry. This level of performance cannot be achieved by simply converting the flow-through processing methods of current systems to software implementations, since a simple addition of all the processing operations needed for one second of real-time imaging in the flow-through architecture gives a number that exceeds the typical number of operations per second currently achievable with several general purpose processors. Consequently, new processing methods are required that achieve a much greater efficiency than the flow-through methods.

Figure 11:
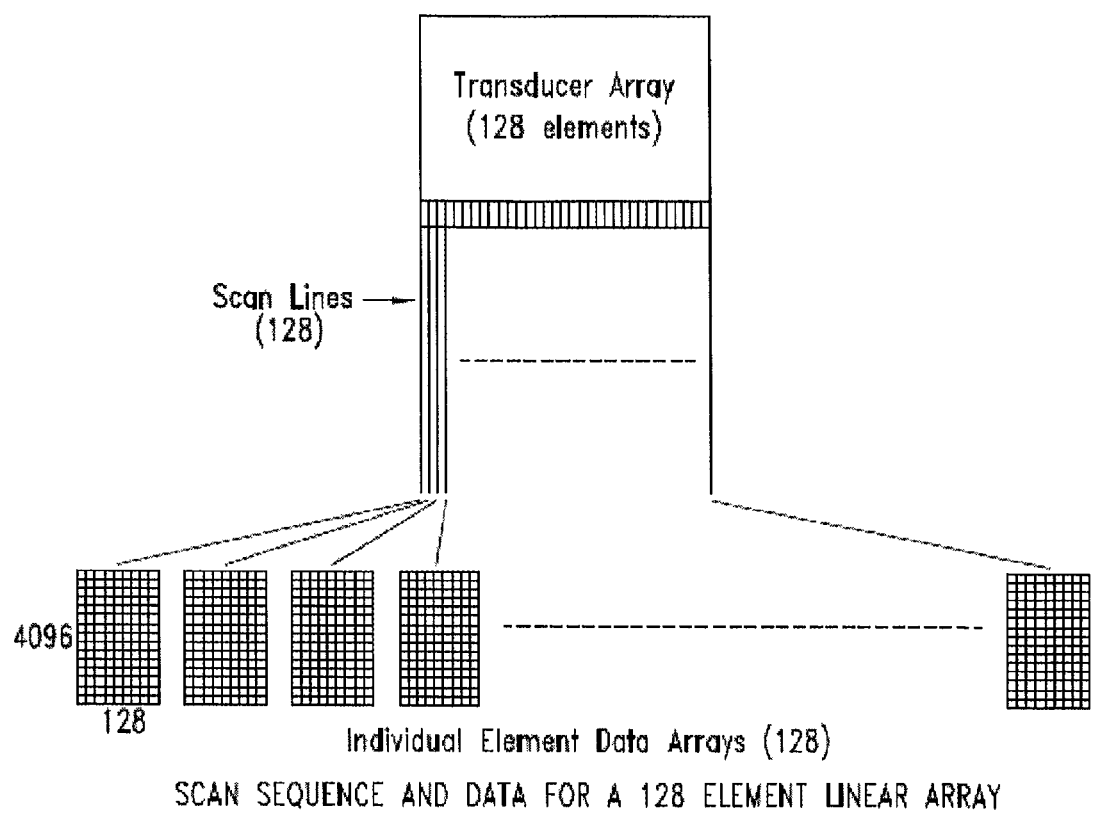
FIG. 11 is a schematic representation of the acquisition data for a 128 element linear array formed in accordance with the pixel-oriented processing.

In one embodiment of the software-based ultrasound system architecture of the present invention, the input data for signal and image processing consists of the set of RF samples acquired from individual transducer channels following one or more transmit events. For an example, let us consider a typical 2D imaging scanning mode with a 128 element linear transducer array, as shown in FIG. 11.

In this case, a 'transmit event' would consist of timed pulses from multiple transducer elements to generate a plurality of acoustic waves that combine in the media to form a focused ultrasound beam that emanates outwards from an origin point on the transducer at a specific element location. Multiple transmit events (128 in all) produce ultrasound beams that are sequentially emitted incrementally across the width of the transducer face, thus interrogating an entire image frame. For each of these transmit beams, the received echo data are collected from each of the 128 receiver elements in the transducer and organized into a data array with each column representing the sampled echo signal received by the corresponding transducer element. Thus, each array has 128 columns, corresponding to the 128 transducer elements, and a number of rows corresponding to the number of samples in depth that were taken (in this case, we will assume 4096 rows resulting in 4096 samples). These 128 data arrays then constitute an RF data set that is sufficient to produce one complete image frame.

It is worth noting that in the flow-through architecture, the RF data set described above does not even exist (at least not all at one time), since the beam and image formation takes place as the data streams in from the transducer. In other words, as the data return to each element after a transmit event, they are processed and combined (referred to as beam forming) to generate a single RF signal representing the focused return along a single beam (scan line). This RF signal is processed (again in real-time) into echo amplitude samples, which are stored in a memory array. When all beam directions have been processed, the echo amplitude data are then interpolated and formatted into a pixel image for display. Since all processing takes place in real-time, the processing circuitry must be able to 'keep up' with the data streaming in from the transducer elements.

In the software-based architecture of the present invention, all input data is stored prior to processing. This uncouples the acquisition rate from the processing rate, allowing the processing time to be longer than the acquisition time, if needed. This is a distinct advantage in high frequency scans, where the depth of acquisition is short and the sample rate high. For example, a 10 MHz scan head might have a useable depth of imaging of around four centimeters. In this case, the speed of sound in tissue dictates that each of the 128 transmit/receive events acquire and store their data in 52 microseconds, a very high acquisition data rate. In the flow-through architecture, these acquisition data would be formed into scan lines in real-time at high processing rates. In the software-based architecture of the present invention, the storage of RF data allows the processing to take as long as the frame period of the display, which for real-time visualization of tissue movement is typically 33 milliseconds (30 frames/second). For 128 pixel columns (the rough analogy to scan lines), this would allow 258 microseconds of processing time per column, rather than the 52 microseconds of the flow-through architecture. This storage strategy has the effect of substantially lowering the maximum rate of processing compared with the flow-through architecture for typical scan depths.

The storing of input data reduces the maximum processing rates but does not necessarily reduce the number of processing steps. To accomplish this, a new approach to ultrasound data processing is taken. The first step is to recognize that the ultimate goal of the system when in an imaging mode is to produce an image on the output display. An ultrasound image has a fundamental resolution that depends on the physical parameters of the acquisition system, such as the frequency and array dimensions, and can be represented as a rectangular array of pixel values that encode echo amplitude or some other tissue (acoustic) property. The density of this rectangular pixel array must provide adequate spatial sampling of the image resolution. It is recognized that display images need not consist only of rectangular arrays of pixels, but could consist of any arbitrary set of pixels, representing different geometric shapes. The next step is to start with one of the pixels in this image array and consider which sample points in the RF data set contribute to the calculation of this pixel's intensity, and determine the most efficient way of accessing and processing them. This approach is a completely different approach than the one utilized by the current flow-through architecture because only information that contributes to pixels on the display needs to be processed. In the approach of the present invention, a small region on the display image will take less overall processing time than a large image region, because the small region contains fewer pixels. In contrast, the flow-through processing methods must be designed to handle the maximum data stream bandwidths, independent of the image region size.

After processing the pixel array required to adequately represent the ultrasound image, the array can be rendered to the computer display at an appropriate size for viewing. The graphics processor of the computer, requiring no additional CPU processing, can typically carry out this operation, which consists of simple scaling and interpolation.

Figure 12:
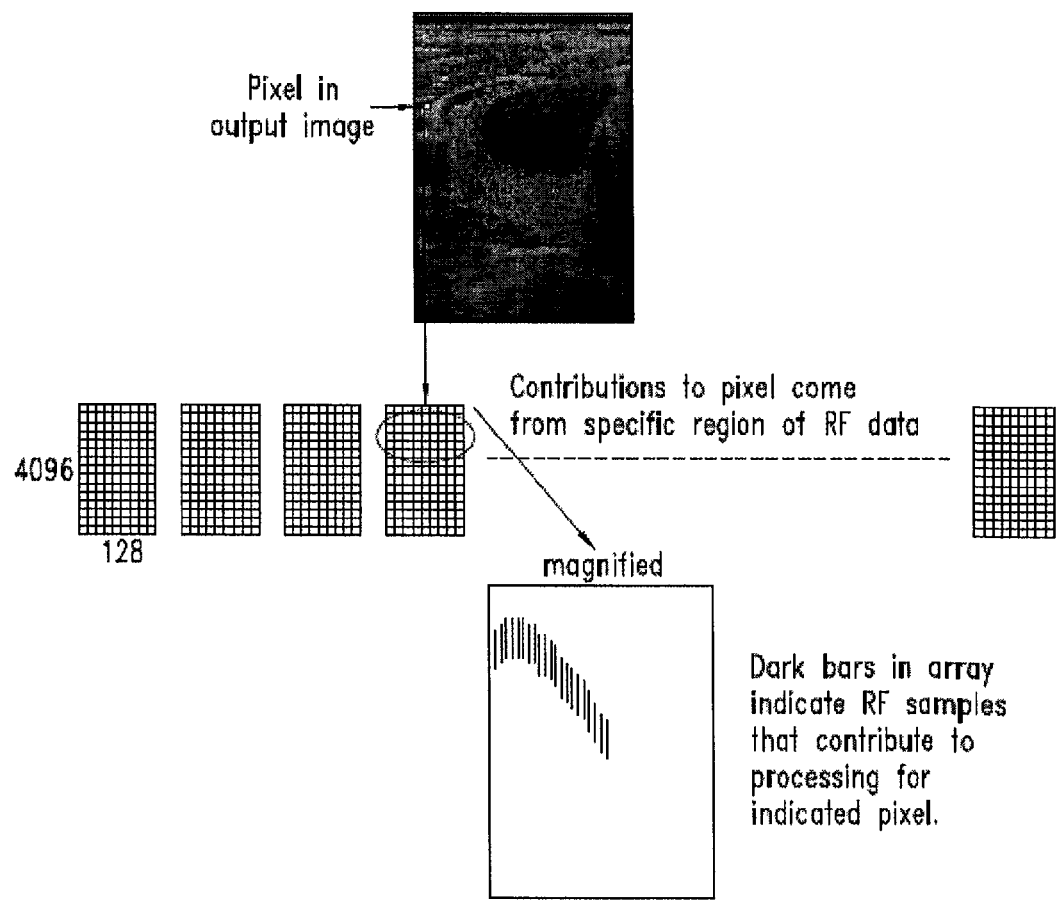
FIG. 12 is an illustration of a pixel mapping process used in pixel-oriented processing.

We next consider the processing strategy for a single pixel of our ultrasound image. In this discussion, we will assume that our objective is to obtain the echo intensity at the corresponding spatial location of the pixel with respect to the transducer array. Other acoustic parameters may be similarly obtained. Our first step is to find the region of acquisition RF data containing samples that contribute to the echo intensity calculation. To accomplish this for the scanning method of FIG. 11, we first find the acquisition scan line that comes closest to intersecting the pixel location, and then use the corresponding individual element data array. FIG. 12 shows this mapping process for an example pixel in an ultrasound image. In FIG. 12, the indicated pixel maps to the closest acquisition line of the scan, which in this case is scan line 4, whose RF data resides in the fourth individual element RF data array (which represents data collected from the fourth transmit/receive event). More than one RF data array could be chosen as contributing to the pixel signal, but for this example we will consider only a single data array.

Out next step is to map out the region in the individual element array containing samples that contribute to the pixel's intensity calculation. This mapping process is fairly complex and depends on several factors. The transducer elements each have a region of sensitivity that determines how they will respond to a signal returning from a particular point in the image field. For a given image point, only elements that have sensitivities above a predetermined threshold need be considered, since if the sensitivity is too low, an element will not contribute useful information to the pixel's quantity. This sensitivity threshold then determines the number of element data columns to include in the mapped region.

The starting depth of the mapped data region or subset is determined by the arrival time of the returning echo at each individual transducer element. As shown in FIG. 12, the image point signal for elements further away from the image point is captured later in time, and so the starting point of the data set is deeper in memory. Finally, the depth range needed for the data in the mapped data region is dependent on the duration of the transmit pulse generated. Longer transmit pulses will excite the image point for a longer period of time, generating echo signals that extend over a larger depth span of the RF memory.

Fortunately, many of the factors that go into determining the region or subset of mapped data for a given pixel can be pre-computed for a given pixel grid, since this grid does not change over the multiple frames of a real-time image sequence. Using pre-computed factors, the mapped data region for a given pixel can be rapidly and efficiently determined, saving considerable computations during real-time imaging.

After selecting out the subset of pixel mapped RF data, we can organize it into a matrix, $RFP_{nm}$, as shown below.

$$RFP_{nm} = \begin{bmatrix} a_{11} a_{12} & \cdots & a_{1k} \\ a_{21} & & \\ \cdots & & \\ \cdots & & \\ a_{j1} & \cdots & a_{jk} \end{bmatrix}$$

The notation '$P_{nm}$' refers to the image pixel in row n, column m. The matrix columns are the vertical bars of FIG. 12 where it is assumed that the number of samples, j, in each vertical bar is the same. The number of samples, j, is dependent on the range of RF data in time needed for capturing the signal generated by the transmit pulse. The index, k, is the number of channels in the RF data array that have adequate signal strength from to the image point to participate in the intensity calculation.

Accordingly, a system using the foregoing can be implemented to carry out the methods, processes, and algorithms of the present disclosure. In one representative embodiment an ultrasound imaging system is provided that includes a module adapted to generate an acoustic signal, receive at least one echo of the acoustic signal at a plurality of receiving elements in the module and obtain a plurality of echo signals therefrom; and a processor coupled to the module. The processor is configured to:

extract information from the plurality of echo signals;

construct a blood flow vector velocity signal using the extracted information by wall filtering the extracted information; using the wall-filtered information to form autocorrelation values and Doppler frequency estimates; partitioning of a bistatic range-rate model with aliasing interference into linear and nonlinear parts; and solving said model by a weighted least squares scheme, the blood flow vector velocity signal corresponding to at least one point in the medium; and detect the presence of blood flow at a display device pixel by qualifying blood flow vector velocity signals through a series of tests on values of quality metrics produced as byproducts of the blood flow vector velocity estimation procedure. A display device is configured to generate blood flow vector velocity imagery from the blood flow vector velocity signals.

In accordance with another aspect of the present disclosure, the system can be provided that includes a module adapted to generate an acoustic signal, receive at least one echo of the acoustic signal at a plurality of receiving elements in the module and obtain a plurality of echo signals therefrom; and a processor coupled to the module. The processor is configured to:

extract information from the plurality of echo signals;

construct a blood flow vector velocity signal using the extracted information by the blood flow vector velocity signal corresponding to at least one point in the medium, the constructing including the following steps of (a) wall filtering the extracted information; (b) using the wall-filtered information to form compressed format conjugate-lagged products; and (c) forming a vector velocity measurement model by using space-time gradient operation on the products, and solving said model by a weighted least squares scheme;

detect the presence of blood flow at a pixel by qualifying blood flow vector velocity signals through a series of tests on values of quality metrics produced as byproducts of the blood flow vector velocity estimation procedure.

A display device is included that is configured to display blood flow vector velocity imagery from the blood flow vector velocity signals.

The various embodiments described above can be combined to provide further embodiments. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method of producing blood flow velocity vector imagery, comprising:

emitting at least two unfocused plane wave acoustic signals M at at least two angles, where M is a number of plane wave acoustic signal emissions, to a transducer array into a medium over substantially an entire field of measurement;

receiving scattered and reflected ultrasonic signals on the transducer array to form received ultrasonic signals in response to the emission;

processing the received ultrasonic signals to generate extracted information for constructing a blood flow vector velocity signal by:

wall filtering the extracted information to generate wall-filtered information;

using the wall-filtered information to form autocorrelation values and Doppler frequency estimates;

partitioning of a bistatic range-rate model into linear and nonlinear parts; and solving the partitioned model by the weighted least squares scheme for the blood flow vector velocity signal v corresponding to at least one point in the medium;

generating blood flow vector velocity signals;

detecting the presence of blood flow corresponding to a display device pixel by qualifying blood flow vector velocity signals through a series of tests on values of quality metrics produced as byproducts of the blood flow vector velocity estimation procedure; and generating on a display device blood flow vector velocity imagery from the blood flow vector velocity signals.

2. The method of claim 1, wherein the emitting and receiving comprise transmitting multiple plane wave acoustic signals and receiving the scattered and reflected ultrasonic signals in ensembles with a timing consistent with Doppler measurements and with a dwell at one or more discrete angles to the transducer array into the medium, with respect to the transducer coordinates, of transmitted plane wave propagation.

3. The method of claim 2, comprising preprocessing the received ultrasonic signals independently for each transmission angle using one or more of wall filtering, auto-correlation, and Doppler frequency estimation.

4. The method of claim 3, comprising assembling Doppler frequency estimates from all transmission angles in a specific bistatic range-rate model and computing an inference of blood flow vector velocity estimates within the field of measurement.

5. The method of claim 4, comprising partitioning of the bistatic range-rate model with aliasing bias vectors into linear and nonlinear parts.

6. The method of claim 5, comprising using variance components as quality estimates for frequency estimates corresponding to each of the plane wave angle data.

7. The method of claim 6, comprising computing Doppler frequency estimate variance, in analogy to the variance of the angle associated with a complex Rice random variable, from Doppler signal-to-noise ratio.

8. The method of claim 6, comprising computing Doppler frequency estimate variance from instantaneous frequency deviates referenced to mean frequency.

9. The method of claim 6, comprising modeling of hypothesized aliasing bias of Doppler frequency and providing consequent corrective adjustments on individual plane wave angle channels affected by aliasing to allow interpretation of aliasing up to twice the pulse rate frequency and prevent image blackout during Doppler aliasing events typically appearing during the systole cardiac phase.

10. The method of claim 9 comprising the providing of restrictions to hypothesized aliasing bias vectors into adjacent plane wave angles, in groups of one or more aliased plane wave angle channels in the model.

11. The method of claim 5 comprising using Doppler frequency variances at each plane wave emission angle to formulate a weighted least squares estimation scheme that computes blood flow vector velocity estimates and an optimal hypothesized aliasing bias vector.

12. The method claim 1, further comprising: performing blood flow detection by qualification tests on by-products of the blood flow vector velocity estimation procedure, comprising:
a. testing computed values of blood flow vector velocity estimate precision;
b. testing computed values of combined power of lag-one autocorrelation values;
c. testing computed values of normalized velocity magnitude;
d. testing computed values of autocorrelation residual; and
e. testing computed values of whitened frequency residual resulting in declaration of pixels being displayed as flow information if qualified by the tests.

13. The method of claim 1, comprising:
correcting a Spectral Doppler image trace frequency scale with a reciprocal of the bistatic range-rate model; and generating on a display device blood flow vector velocity imagery from the blood flow vector velocity signals as a quantitative blood velocity spectrum from the correcting of the Spectral Doppler image trace frequency scale.

14. The method of claim 1, comprising:
generating on a display device blood flow vector velocity imagery from the blood flow vector velocity signal, as quantitative instantaneous blood flow rate by:
integrating blood flow velocity vectors, projected to the surface normal, over a voxel surface slicing the vessel; and
displaying the result as instantaneous flow rate, on a format analogous to Spectral Doppler Image, with the vertical axis labeled in flow rate units.

15. The method of claim 1, comprising:
generating on a display device blood flow vector velocity imagery from the blood flow vector velocity signal, by synthetic particle entrainment with independent particle processing, the steps including:
adjusting particle density to follow dynamics of flow extent from frame to frame, for multiple unconnected flow regions;
testing for particles leaving flow region, and responding to the affirmative by deleting relevant particles from particle list;
testing for particles entering flow regions, and responding to the affirmative by creating particles in associated pixels probabilistically;
propagating each particle in the particle list forward in time by advancing its spatial position according to its nearest coincident blood flow vector velocity estimate; and
scaling of the collection of displayed particle propagation velocities by a desired "slowdown" factor to enable viewing of particle flow paths at an arbitrarily reduced speed.

16. The method of claim 1, wherein the partitioning of the bistatic range rate model comprises the model $f=Av+b+e$, wherein v is a blood flow velocity vector at an image point and $v=[\sigma_x, \sigma_z]_T$, b represents bias due to aliasing and is equal to 0 when there is no biasing, e is stochastic error, and the model matrix A is dimensioned [M×2] and has rows $\alpha_m(\theta_m)$, where:

$$a_m = \frac{1}{\lambda}[\sin(\theta_m), 1 + \cos(\theta_m)]$$

with explicit terms for bias due to aliasing of Doppler frequencies.

17. An ultrasound processing system, comprising:
a module adapted to generate an acoustic signal, receive at least one echo of the acoustic signal at a plurality of receiving elements in the module and obtain a plurality of echo signals therefrom; and
a processor coupled to the module and configured to:
extract information from the plurality of echo signals to construct a blood flow vector velocity signal by:
wall filtering the extracted information;

using the wall-filtered information to form autocorrelation values and Doppler frequency estimates;

partitioning of a bistatic range-rate model into linear and nonlinear parts; and solving the partitioned model by the weighted least squares scheme corresponding to at least one point in the medium; and detect the presence of blood flow at a display device pixel by qualifying blood flow vector velocity signals through a series of tests on values of quality metrics produced as byproducts of the blood flow vector velocity estimation procedure; and a display device configured to generate blood flow vector velocity imagery from the blood flow vector velocity signals.

18. The system of claim 17 wherein the partitioning of the bistatic range rate model comprises the model f=Av+b+e, wherein v is a blood flow velocity vector at an image point and v=$[\sigma_x, \sigma_z]_T$, b represents bias due to aliasing and is equal to 0 when there is no biasing, e is stochastic error, and the model matrix A is dimensioned [M×2] and has rows $\alpha_m(\theta_m)$, where:

$$a_m = \frac{1}{\lambda}[\sin(\theta_m), 1 + \cos(\theta_m)]$$

with explicit terms for bias due to aliasing of Doppler frequencies.

* * * * *